US011060106B2

(12) United States Patent
Mathur et al.

(10) Patent No.: US 11,060,106 B2
(45) Date of Patent: Jul. 13, 2021

(54) CYTOPLASMIC MALE STERILITY GENE ORF147 OF PIGEONPEA, AND USES THEREOF

(71) Applicant: INTERNATIONAL CROPS RESEARCH INSTITUTE FOR THE SEMI-ARID TROPICS (ICRISAT), Hyderabad (IN)

(72) Inventors: Pooja Bhatnagar Mathur, Hyderabad (IN); Kiran Kumar Sharma, Hyderabad (IN); Ranadheer Kumar Gupta, Hyderabad (IN)

(73) Assignee: INTERNATIONAL CROPS RESEARCH INSTITUTE FOR THE SEMI- ARID TROPICS (ICRISAT), Hyderabad (IN)

( * ) Notice: Subject to any disclaimer, the term of this patent is extended or adjusted under 35 U.S.C. 154(b) by 87 days.

(21) Appl. No.: 16/465,517

(22) PCT Filed: Dec. 1, 2017

(86) PCT No.: PCT/IN2017/050564
§ 371 (c)(1),
(2) Date: May 31, 2019

(87) PCT Pub. No.: WO2018/100590
PCT Pub. Date: Jun. 7, 2018

(65) Prior Publication Data
US 2019/0382789 A1    Dec. 19, 2019

(30) Foreign Application Priority Data
Dec. 2, 2016 (IN) .............................. 201641041375

(51) Int. Cl.
C12N 15/82    (2006.01)
C07K 14/415   (2006.01)
C12Q 1/6895   (2018.01)

(52) U.S. Cl.
CPC ........ C12N 15/8289 (2013.01); C07K 14/415 (2013.01); C12Q 1/6895 (2013.01); C12Q 2600/13 (2013.01)

(58) Field of Classification Search
CPC ................................................ C12N 15/8289
See application file for complete search history.

(56) References Cited

PUBLICATIONS

Tuteja, R. et al., DNA Research; vol. 20, pp. 485-495 (2013) (Year: 2013).*
Bohra, A. et al. (2016, c-pub. Feb. 23, 2016). "Cytoplasmic Male Sterility (CMS) in Hybrid Breeding in Field Crops," Plant Cell Reports 35:967-993.
Clough, S.J. et al. (Dec. 1998). "Floral Dip: A Simplified Method for Agrobacterium-Mediated Transformation of *Arabidopsis thaliana*," Plant J. 16(6):735-743.
Czechowski, T. et al. (Sep. 2005), Genome-Wide Identification and Testing of Superior Reference Genes for Transcript Normalization in *Arabidopsis*. Plant Physiol. 139(1):5-17.
Dewey, R.E. et al. (Feb. 14, 1986), "Novel Recombinations in The Maize Mitochondrial Genome Produce A Unique Transcriptional Unit in the Texas Male-Sterile Cytoplasm," Cell 44(3):439-449.
Duroc, Y. et al. (Dec. 2005, c-pub. Jun. 9, 2005). "Biochemical and Functional Characterization of ORF138, A Mitochondrial Protein Responsible for Ogura Cytoplasmic Male Sterility in *Brassiceae*," Biochimie 87(12):1089-1100.
Genbank CBX24958—"Hypothetical Protein (Mitochondrion) [Beta Macrocarpa]," 1 page.
Hanson, M.R. et al. (2004). "Interactions of Mitochondrial and Nuclear Genes That Affect Male Gametophyte Development," The Plant Cell 16(Suppl. S):S154-S169.
Hellemans, J. et al. (Feb. 9, 2007). "qBase Relative Quantification Framework and Software for Management and Automated Analysis of Real-Time Quantitative PCR Data," Genome Biol. 8(2):R19, 14 pages.
International Preliminary Report on Patentability, dated Jun. 4, 2019, for PCT Application No. PCT/IN2017/050564, filed Dec. 1, 2017, 8 pages.
International Search Report and Written Opinion, dated Apr. 9, 2018, for PCT Application No. PCT/CN2017/050564, filed Dec. 1, 2017, 12 pages.
Iwabuchi, M. et al. (Jan. 1999). "Identification and Expression of The Kosena Radish (*Raphanus sativus* cv. Kosena) Homologue of the Ogura Radish CMS-Associated Gene, orf138," Plant Mol, Biol. 39(1):183-188.
Jack, T. et al. (Feb. 25, 1994). "*Arabidopsis* Homeotic Gene APETALA3 Ectopic Expression: Transcriptional and Post-transcriptionai Regulation Determine Floral Organ Identity," Cell 76(4):703-716.
Jing, B. et al. (Feb. 2012, e-pub. Nov. 16, 2011). "A Male Sterility-Associated Cytotoxic Protein ORF288 in *Brassica juncea* Causes Aborted Pollen Development," J. Exp, Bot. 63(3):1285-1295.
Köhler, R.H. et al. (1991). "Cytoplasmic Male Sterility in Sunflower is Correlated Wath the Co-Transcription of a New Open Reading Frame with atpA Gene," Mol. Gen. Genet. 227:369-376.
Landgren, M. et al, (Dec. 1996), "Alloplasmic Male-Sterile *Brassica* Lines Containing B. tournefortii Mitochondria Express an ORF 3' of the atp6 Gene and a 32 kDa Protein," Plant Mol. Bio. 32(5):879-890.
Laver, H.K. et al. (Sep. 1991). "Mitochondrial Genome Organization and Expression Associated With Cytoplasmic Male Sterility in Sunflower (*Helianthus annuus*)," Plant J. 1(2):185-193.

(Continued)

Primary Examiner — Russell Kallis
(74) Attorney, Agent, or Firm — Morrison & Foerster LLP

(57) ABSTRACT

The present disclosure provides, a DNA construct comprising a polynucleotide fragment comprising a first, and a second sequence, wherein said first sequence encodes a mitochondrial transit peptide, said second sequence encodes a polypeptide having amino acid sequence as set forth in SEQ ID NO: 1, and said polynucleotide fragment is operably linked to a flower specific promoter. The present disclosure also provides with a DNA vector, a recombinant host cell and a method of obtaining the same.

15 Claims, 9 Drawing Sheets
Specification includes a Sequence Listing.

(56) References Cited

PUBLICATIONS

Mackenzie, S. et al. (Apr. 1999). "Higher Plant Mitochondria," Plant Cell 11(4):571-585.

Nivison, H.T, et al. (Nov. 1989)."Identification of A Mitochondrial Protein Associated With Cytoplasmic Male Sterility in Petunia," Plant Cell 1(11):1121-1130.

Pranathi, K. et al. (Feb. 16, 2016), "Comparative Analysis of Sequences of Mitochondrial Genomes of Wild Abortive Male Sterile (WA-CMS) and Male Fertile Lines of Rice, Development of Functional Markers for WA-CMS Trait and Their Use in Assessment of Genetic Purity of Seeds of WA-CMS Lines," Molecular Breeding: New Strategies in Plant Improvement 36:21, 12 pages.

Reddy, P.S. et al. (Oct. 15, 2008, e-pub. Jul. 22, 2008). "A High-Throughput Genorne-Walking Method and Its Use for Cloning Unknown Flanking Sequences," Anal. Biochem. 381(2):248-253.

Saxena, K.B. et al. (Jul.-Aug. 2010, e-pub. Apr. 9, 2010). "Development of Cytoplasmic-Nuclear Male Sterility, its Inheritance, and Potential Use in Hybrid Pigeonpea Breeding," J. Hered 101(4):497-503.

Saxena, K.B. et al. (Oct. 2005). "A Cytoplasmic-Nuclear Male-Sterility System Derived From A Cross Between Cajanus cajanifolius and Cajanus cajan." Euphytica. 145(3):289-294.

Sinha, P. et al. (Jul. 10, 2015). "Association of nad7a Gene with Cytoplasmic Male Sterility in Pigeonpea", The Plant Genome 8(2):1-2.

Sunkara, S. et al. (2014, e-pub. Sep. 29, 2013). "Isolation and Functional Characterization of a Novel Seed-Specific Promoter Region from Peanut," Appl. Biochem. Biotechnol. 172:325-339.

Tuteja, R. et al. (Oct. 2013, e-pub. Jun. 20, 2013). "Cytopiasmic Male Sterility-Associated Chimeric Open Reading Frames identified by Mitochondrial Genome Sequencing of Four Cajanus Genotypes," DNA Res. 20 (5):485-495.

Wang, Z. (Mar. 2006). "Cytoplasmic Male Sterility of Rice with Baro II Cytoplasm Is Caused by a Cytotoxic Peptide and Is Restored by Two Related PPR Motif Genes via Distinct Modes of mRNA Silencing," The Plant Cell 18 (3):676-687.

Young, E.G. et al. (Jul. 1987). "A Fused Mitochondrial Gene Associated With Cytoplasmic Male Sterility Is Developmentally Regulated," Cell 50(1):41-49.

Genbank AHW58030.1—"AP3 [Coffea arabica]," 2 pages.

Genbank AM261325.1—"Lycopersicon esculentum Partial to-29 Gene, Clone TA-295N1," 1 page.

Genbank DQ539418.1—"Lycopersicon esculentum AP3 (AP3) Gene, Promoter Region and Partial Cds," 2 pages.

Genpept P0403711-25—"RecNarne: Full=Cytochrorne c Oxidase Subunit 4, Mitochondrial; AltName: Full=Cytochrome c Oxidase Polypeptide IV; Flags; Precursor," 3 pages.

Genbank U30729.1—*Arabidopsis thaliana* Floral Homeotic (AP3) Gene, Promoter Region and Partial Cds," 2 pages.

Genbank X52283.1—"Tobacco Anther-Specific Gene TA-29 and Stem-Specific Gene TSJT1," 3 pages.

\* cited by examiner

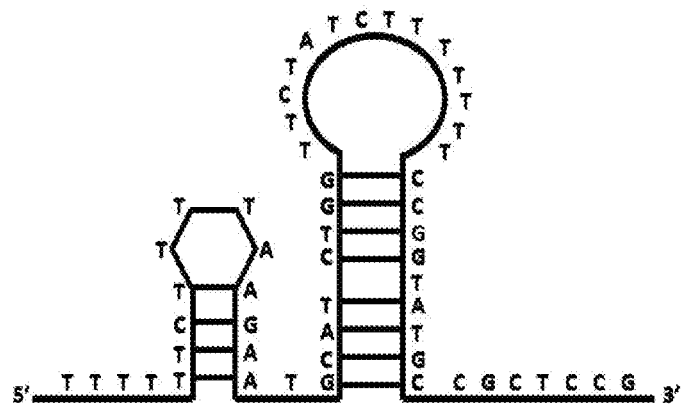
Figure 4A
MHLVLSFFPVCRSASKERKLKANKDKMTREIKLYVDTTPSDLDFMMNSDTDLQSLSSPDSSDAQSA
SPDLDLLWDQVCGEYHKCVHESGRVLPPEWTMPDLVRAVISDDEAIEQGFLTDAYYDVMLCGTHS
WVCEELLNFLDLIHYG*
Figure 4B
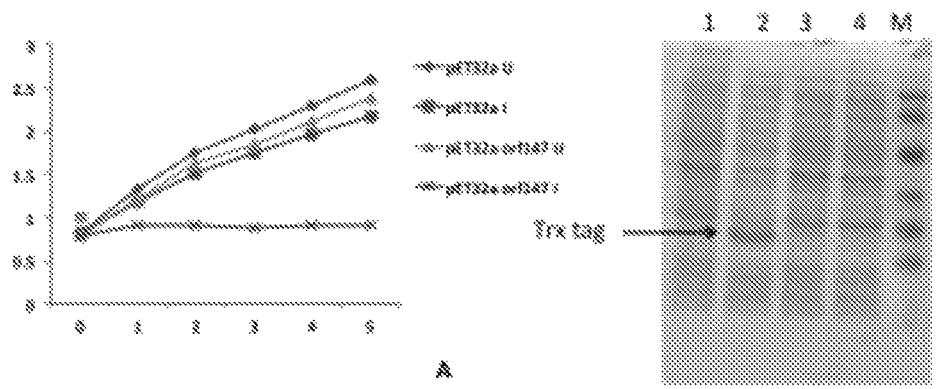
Figure 5A

Figure 6B-J

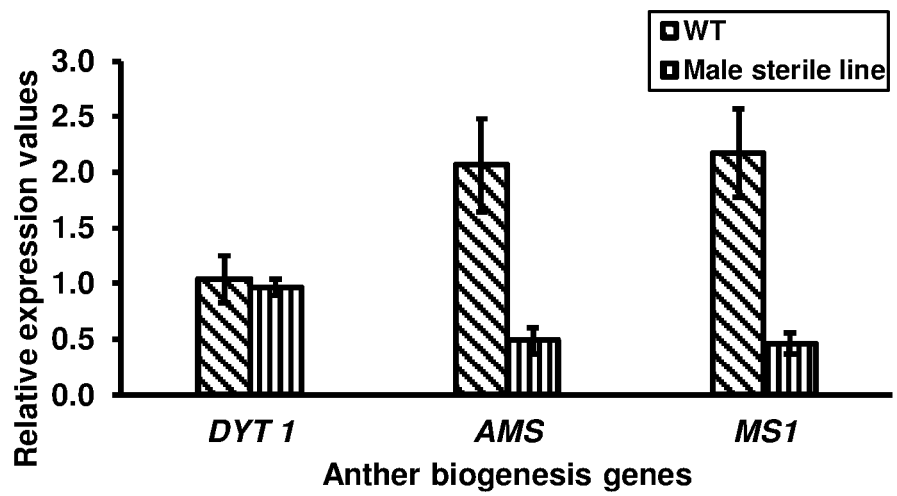
Figure 8B
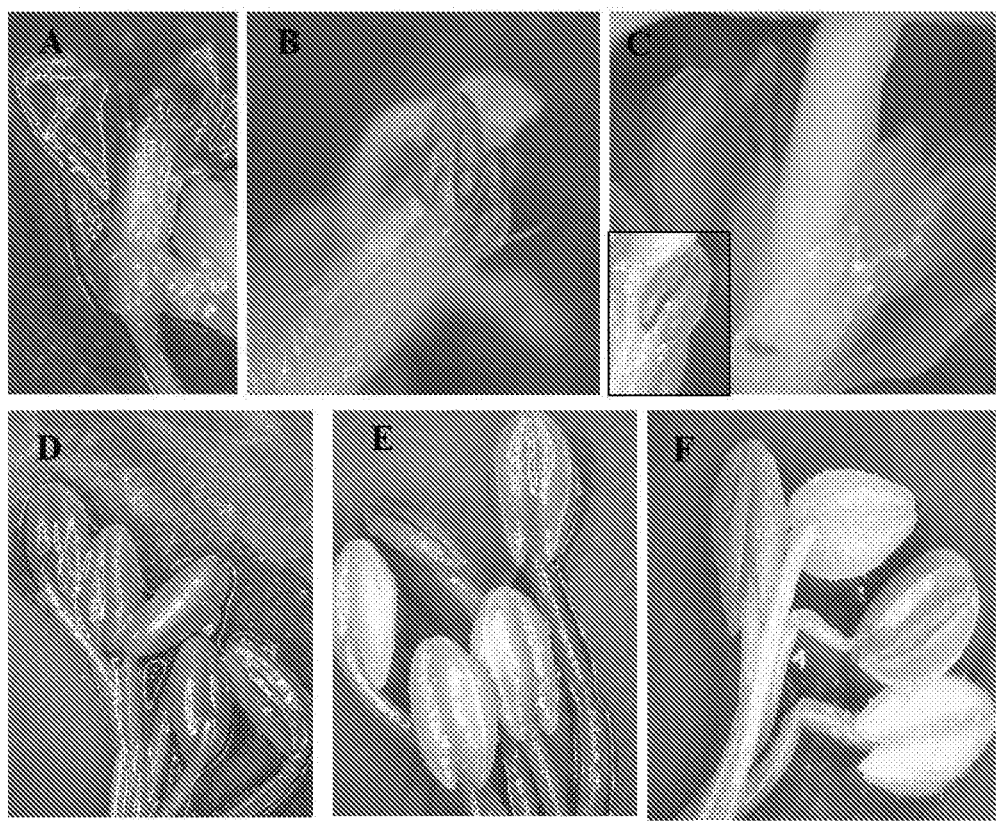
Figure 9A-F

SEQUENCE LISTING

```
<160> NUMBER OF SEQ ID NOS: 51

<210> SEQ ID NO 1
<211> LENGTH: 147
<212> TYPE: PRT
<213> ORGANISM: Artificial Sequence
<220> FEATURE:
<223> OTHER INFORMATION: orf147 Polypeptide

<400> SEQUENCE: 1
```

```
Met His Leu Val Leu Ser Phe Phe Pro Val Cys Arg Ser Ala Ser Lys
1               5                   10                  15

Glu Arg Lys Leu Lys Ala Asn Lys Asp Lys Met Thr Arg Glu Ile Lys
            20                  25                  30

Leu Tyr Val Asp Thr Thr Pro Ser Asp Leu Asp Phe Met Met Asn Ser
        35                  40                  45

Asp Thr Asp Leu Gln Ser Leu Ser Ser Pro Ser Ser Asp Ala Gln
    50                  55                  60

Ser Ala Ser Pro Asp Leu Asp Leu Leu Trp Asp Gln Val Cys Gly Glu
65              70                  75                  80

Tyr His Lys Cys Val His Glu Ser Gly Arg Val Leu Pro Pro Glu Trp
                85                  90                  95

Thr Met Pro Asp Leu Val Arg Ala Val Ile Ser Asp Asp Glu Ala Ile
            100                 105                 110

Glu Gln Gly Phe Leu Thr Asp Ala Tyr Tyr Asp Val Met Leu Cys Gly
                115                 120                 125

Thr His Ser Trp Val Cys Glu Glu Leu Leu Asn Phe Leu Asp Leu Ile
    130                 135                 140

His Tyr Gly
145

<210> SEQ ID NO 2
<211> LENGTH: 29
<212> TYPE: PRT
<213> ORGANISM: Artificial Sequence
<220> FEATURE:
<223> OTHER INFORMATION: Mitochondrial transit peptide

<400> SEQUENCE: 2

Met Leu Ser Leu Arg Gln Ser Ile Arg Phe Phe Lys Pro Ala Thr Arg
1               5                   10                  15

Thr Leu Cys Ser Ser Arg Tyr Leu Leu Gln Gln Lys Pro
            20                  25

<210> SEQ ID NO 3
<211> LENGTH: 444
<212> TYPE: DNA
<213> ORGANISM: Artificial Sequence
<220> FEATURE:
<223> OTHER INFORMATION: orf17 DNA

<400> SEQUENCE: 3
atgcatctgg ttctatcttt ttttccggta tgccgctccg ccagcaagga gcgaaaacta      60
aaagcaaaca agataagat gaccagagag atcaagctat atgtggatac cacccctagt     120
gatttggatt ttatgatgaa tagtgatacg gatttgcagt ccttgtcttc cccggattcg     180
tccgacgcac agagtgcttc accggacttg gacctattat gggatcaagt tgtggtgaa     240 taccacaagt gtgtgcatga atccggggagg gtcttacccc cggaatggac gatgcccgac     300
cttgttcggg ctgttatttc cgacgatgaa gctattgagc agggctttct gacggatgcc     360
tactatgatg tcatgttatg tggcactcat agttgggtat gcgaggagct gcttaatttc     420
ctcgatctaa tccactatgg ctga                                            444

<210> SEQ ID NO 4
<211> LENGTH: 87
<212> TYPE: DNA
<213> ORGANISM: Artificial Sequence
<220> FEATURE:
```

<223> OTHER INFORMATION: Mitochondrial transit DNA

<400> SEQUENCE: 4

```
atgttgtcac tacgtcaatc tataagattt ttcaagccag ccacaagaac tttgtgtagc    60
tctagatatc tgcttcagca aaaccc                                          87
```

<210> SEQ ID NO 5
<211> LENGTH: 869
<212> TYPE: DNA
<213> ORGANISM: Artificial Sequence
<220> FEATURE:
<223> OTHER INFORMATION: Arabidopsis promoter sequence

<400> SEQUENCE: 5

```
cagtaactgt ggccaactta gttttgaaac aacactaact ggtcgaagca aaagaaaaa     60
agagtttcat catatatctg atttgatgga ctgtttggag ttaggaccaa acattatcta   120
caaacaaaga cttttctcct aacttgtgat tccttcttaa accctagggg taatattcta   180
ttttccaagg atctttagtt aaaggcaaat ccgggaaatt attgtaatca tttggggaaa   240
catataaaag atttgagtta gatggaagtg acgattaatc caaacatata tatctctttc   300
ttcttatttc ccaaattaac agacaaaagt agaatattgg cttttaacac aatataaaa    360
acttgttcac acctaaacac ttttgtttac tttagggtaa gtgtaaaaag ccaaccaaat   420
ccacctgcac tgatttgacg tttacaaacg ccgttaagtt tgtcaccgtc taaacaaaaa   480
caaagtagaa gctaacggag ctccgttaat aaattgacga aaagcaaacc aagtttttag   540
ctttggtccc cctcttttac caagtgacaa ttgatttaag cagtgtcttg taattataca   600
accatcgatg tccgttgatt taaacagtgt cttgtaatta aaaaaatcag tttacataaa   660
tggaaaattt atcacttagt tttcatcaac ttctgaactt acctttcatg gattaggcaa   720
tactttccat ttttagtaac tcaagtggac cctttacttc ttcaactcca tctctctctt   780
tctatttcac ttctttcttc tcattatatc tcttgtcctc tccaccaaat ctcttcaaca   840
aaaagattaa acaaagagag aagaatcat                                     869
```

<210> SEQ ID NO 6
<211> LENGTH: 176
<212> TYPE: PRT
<213> ORGANISM: Artificial Sequence
<220> FEATURE:
<223> OTHER INFORMATION: Mitochonrial transit peptide fused to orf147

<400> SEQUENCE: 6

```
Met Leu Ser Leu Arg Gln Ser Ile Arg Phe Phe Lys Pro Ala Thr Arg
1               5                   10                  15

Thr Leu Cys Ser Ser Arg Tyr Leu Leu Gln Gln Lys Pro Met His Leu
            20                  25                  30

Val Leu Ser Phe Phe Pro Val Cys Arg Ser Ala Ser Lys Glu Arg Lys
        35                  40                  45

Leu Lys Ala Asn Lys Asp Lys Met Thr Arg Glu Ile Lys Leu Tyr Val
    50                  55                  60

Asp Thr Thr Pro Ser Asp Leu Asp Phe Met Met Asn Ser Asp Thr Asp
65                  70                  75                  80

Leu Gln Ser Leu Ser Phe Pro Asp Ser Ser Asp Ala Gln Ser Ala Ser
                85                  90                  95

Pro Asp Leu Asp Leu Leu Trp Asp Arg Val Cys Gly Glu Tyr His Lys
            100                 105                 110
```

```
Cys Val His Glu Ser Gly Arg Val Leu Pro Pro Glu Trp Thr Met Pro
            115                 120                 125

Asp Leu Val Arg Ala Val Ile Ser Asp Asp Glu Ala Ile Glu Gln Gly
        130                 135                 140

Phe Leu Thr Asp Ala Tyr Tyr Asp Val Met Leu Cys Gly Thr His Ser
145                 150                 155                 160

Trp Val Cys Glu Glu Leu Leu Asn Phe Leu Asp Leu Ile His Tyr Gly
                165                 170                 175

<210> SEQ ID NO 7
<211> LENGTH: 531
<212> TYPE: DNA
<213> ORGANISM: Artificial Sequence
<220> FEATURE:
<223> OTHER INFORMATION: Mitochondrial transit peprtide fused to orf147
      DNA

<400> SEQUENCE: 7
atgttgtcac tacgtcaatc tataagattt ttcaagccag ccacaagaac tttgtgtagc      60
tctagatatc tgcttcagca aaaacccatg catctggttc tatcttttt tccggtatgc     120 cgctccgcca gcaaggagcg aaaactaaaa gcaaacaaag ataagatgac cagagagatc     180
aagctatatg tggataccac ccctagtgat ttggatttta tgatgaatag tgatacggat     240
ttgcagtcct tgtctttccc ggattcgtct gacgcacaga gtgcttcacc ggacttggac     300
ctattatggg atcgagtttg tggtgaatac cacaagtgtg tgcatgaatc cgggagggtc     360 ttaccccgg aatggacgat gcccgacctt gttcgggctg ttatttccga cgatgaagct     420
attgagcagg gctttctgac ggatgcctac tatgatgtca tgttatgtgg cactcatagt     480
tgggtatgcg aggagctgct taatttcctc gatctaatcc actatggctg a             531

<210> SEQ ID NO 8
<211> LENGTH: 20
<212> TYPE: DNA
<213> ORGANISM: Artificial Sequence
<220> FEATURE:
<223> OTHER INFORMATION: Antisense primer sequence for genome walking

<400> SEQUENCE: 8
aattcaaagt gaaattttg                                                   20

<210> SEQ ID NO 9
<211> LENGTH: 23
<212> TYPE: DNA
<213> ORGANISM: Artificial Sequence
<220> FEATURE:
<223> OTHER INFORMATION: Forward primer sequence orf133

<400> SEQUENCE: 9
atgcagttac tctttgagtt gga                                              23

<210> SEQ ID NO 10
<211> LENGTH: 23
<212> TYPE: DNA
<213> ORGANISM: Artificial Sequence
<220> FEATURE:
<223> OTHER INFORMATION: Reverse primer sequence orf133

<400> SEQUENCE: 10
tcatgctctt aacttacctt ctg                                              23

<210> SEQ ID NO 11
```

```
<211> LENGTH: 19
<212> TYPE: DNA
<213> ORGANISM: Artificial Sequence
<220> FEATURE:
<223> OTHER INFORMATION: Forward primer sequence orf147

<400> SEQUENCE: 11
atgcatctgg ttctatctt                                                19

<210> SEQ ID NO 12
<211> LENGTH: 24
<212> TYPE: DNA
<213> ORGANISM: Artificial Sequence
<220> FEATURE:
<223> OTHER INFORMATION: Reverse primer sequence orf147

<400> SEQUENCE: 12
tcagccatag tggattagat cgag                                          24

<210> SEQ ID NO 13
<211> LENGTH: 24
<212> TYPE: DNA
<213> ORGANISM: Artificial Sequence
<220> FEATURE:
<223> OTHER INFORMATION: Forward primer sequence with NdeI restriction
      site for orf133

<400> SEQUENCE: 13
tcagccatag tggattagat cgag                                          24

<210> SEQ ID NO 14
<211> LENGTH: 32
<212> TYPE: DNA
<213> ORGANISM: Artificial Sequence
<220> FEATURE:
<223> OTHER INFORMATION: Reverse primer sequence with SalI restriction
      site for orf133

<400> SEQUENCE: 14
atagtcgact catgctctta acttaccttc tg                                 32

<210> SEQ ID NO 15
<211> LENGTH: 25
<212> TYPE: DNA
<213> ORGANISM: Artificial Sequence
<220> FEATURE:
<223> OTHER INFORMATION: Forward primer sequence with NdeI restriction
      site for orf147

<400> SEQUENCE: 15
tatcatatgc atctggttct atctt                                         25

<210> SEQ ID NO 16
<211> LENGTH: 31
<212> TYPE: DNA
<213> ORGANISM: Artificial Sequence
<220> FEATURE:
<223> OTHER INFORMATION: Forward primer sequence with SalI restriction
      site for orf147

<400> SEQUENCE: 16
tatgtcgact cagccatagt ggattagatc g                                  31

<210> SEQ ID NO 17
<211> LENGTH: 31
<212> TYPE: DNA
<213> ORGANISM: Artificial Sequence
```

```
<220> FEATURE:
<223> OTHER INFORMATION: Forward primer with KpnI site for amplifying
      AtAP3 promoter

<400> SEQUENCE: 17
taggtaccca gtaactgtgg ccaacttagt t                                    31

<210> SEQ ID NO 18
<211> LENGTH: 35
<212> TYPE: DNA
<213> ORGANISM: Artificial Sequence
<220> FEATURE:
<223> OTHER INFORMATION: Reverse primer with NdeI site for amplifying
      AtAP3 promoter

<400> SEQUENCE: 18
tcagatcata tgattcttct ctctttgttt aatct                                35

<210> SEQ ID NO 19
<211> LENGTH: 26
<212> TYPE: DNA
<213> ORGANISM: Artificial Sequence
<220> FEATURE:
<223> OTHER INFORMATION: Forward primer for amplifying CoxIV
      mitochondrial signal peptide

<400> SEQUENCE: 19
atgttgtcac tacgtcaatc tataag                                          26

<210> SEQ ID NO 20
<211> LENGTH: 20
<212> TYPE: DNA
<213> ORGANISM: Artificial Sequence
<220> FEATURE:
<223> OTHER INFORMATION: Reverse primer for amplifying CoxIV
      mitochondrial signal peptide

<400> SEQUENCE: 20 gggttttttgc tgaagcagat                                                20

<210> SEQ ID NO 21
<211> LENGTH: 45
<212> TYPE: DNA
<213> ORGANISM: Artificial Sequence
<220> FEATURE:
<223> OTHER INFORMATION: Forward primer for amplifying CoxIV orf147
      fusion

<400> SEQUENCE: 21
atctgcttca gcaaaaaccc atgcatctgg ttctatcttt ttttc                     45

<210> SEQ ID NO 22
<211> LENGTH: 45
<212> TYPE: DNA
<213> ORGANISM: Artificial Sequence
<220> FEATURE:
<223> OTHER INFORMATION: Reverse primer for amplifying CoxIV orf147
      fusion

<400> SEQUENCE: 22
gaaaaaaaga tagaaccaga tgcatgggtt tttgctgaag cagat                     45

<210> SEQ ID NO 23
<211> LENGTH: 32
<212> TYPE: DNA
<213> ORGANISM: Artificial Sequence
<220> FEATURE:
```

<223> OTHER INFORMATION: Forward primer with NdeI restriction site for
      amplifying CoxIV orf147 fusion

<400> SEQUENCE: 23
tatcatatgt tgtcactacg tcaatctata ag                                32

<210> SEQ ID NO 24
<211> LENGTH: 30
<212> TYPE: DNA
<213> ORGANISM: Artificial Sequence
<220> FEATURE:
<223> OTHER INFORMATION: Reverse primer with NotI restriction site for
      amplifying CoxIV orf147 fusion

<400> SEQUENCE: 24
gcggccgctc agccatagtg gattagatcg                                   30

<210> SEQ ID NO 25
<211> LENGTH: 22
<212> TYPE: DNA
<213> ORGANISM: Artificial Sequence
<220> FEATURE:
<223> OTHER INFORMATION: Forward primer sequence for amplifying DYT1

<400> SEQUENCE: 25
gaagctcctc ctgagattga tg                                           22

<210> SEQ ID NO 26
<211> LENGTH: 22
<212> TYPE: DNA
<213> ORGANISM: Artificial Sequence
<220> FEATURE:
<223> OTHER INFORMATION: Reverse primer sequence for amplifying DYT1

<400> SEQUENCE: 26
cttcctctcc ccaatcttac ac                                           22

<210> SEQ ID NO 27
<211> LENGTH: 22
<212> TYPE: DNA
<213> ORGANISM: Artificial Sequence
<220> FEATURE:
<223> OTHER INFORMATION: Forward primer sequence for amplifying AMS

<400> SEQUENCE: 27
aggctctatg caaaacgaaa ag                                           22

<210> SEQ ID NO 28
<211> LENGTH: 22
<212> TYPE: DNA
<213> ORGANISM: Artificial Sequence
<220> FEATURE:
<223> OTHER INFORMATION: Reverse primer sequence for amplifying AMS

<400> SEQUENCE: 28
ggttgtggta atggttgatg tg                                           22

<210> SEQ ID NO 29
<211> LENGTH: 22
<212> TYPE: DNA
<213> ORGANISM: Artificial Sequence
<220> FEATURE:
<223> OTHER INFORMATION: Forward primer sequence for amplifying SAND

<400> SEQUENCE: 29
gtgcagacac aaggttgtca gt                                           22

<210> SEQ ID NO 30
<211> LENGTH: 22
<212> TYPE: DNA
<213> ORGANISM: Artificial Sequence
<220> FEATURE:
<223> OTHER INFORMATION: Reverse primer sequence for amplifying SAND

<400> SEQUENCE: 30
ggtaggcaga ttggtgagaa ag                                          22

<210> SEQ ID NO 31
<211> LENGTH: 22
<212> TYPE: DNA
<213> ORGANISM: Artificial Sequence
<220> FEATURE:
<223> OTHER INFORMATION: Forward primer sequence for amplifying TIP41

<400> SEQUENCE: 31
gaagatgagg caccaactgt tc                                          22

<210> SEQ ID NO 32
<211> LENGTH: 22
<212> TYPE: DNA
<213> ORGANISM: Artificial Sequence
<220> FEATURE:
<223> OTHER INFORMATION: Reverse primer sequence for amplifying TIP41

<400> SEQUENCE: 32
gcttaatcac tggaagcctc tg                                          22

<210> SEQ ID NO 33
<211> LENGTH: 22
<212> TYPE: DNA
<213> ORGANISM: Artificial Sequence
<220> FEATURE:
<223> OTHER INFORMATION: Forward primer sequence for amplifying UNK

<400> SEQUENCE: 33
gctgagaagc atgttcagga gt                                          22

<210> SEQ ID NO 34
<211> LENGTH: 22
<212> TYPE: DNA
<213> ORGANISM: Artificial Sequence
<220> FEATURE:
<223> OTHER INFORMATION: Reverse primer sequence for amplifying UNK

<400> SEQUENCE: 34
gttcatgagc tcagagagac ca                                          22

<210> SEQ ID NO 35
<211> LENGTH: 22
<212> TYPE: DNA
<213> ORGANISM: Artificial Sequence
<220> FEATURE:
<223> OTHER INFORMATION: Forward primer sequence for amplifying C3H

<400> SEQUENCE: 35
agttcgacag agtggttgga ct                                          22

<210> SEQ ID NO 36
<211> LENGTH: 22
<212> TYPE: DNA
<213> ORGANISM: Artificial Sequence
<220> FEATURE:

<223> OTHER INFORMATION: Reverse primer sequence for amplifying C3H

<400> SEQUENCE: 36
gcttcggtga ggtagcatta ga                                              22

<210> SEQ ID NO 37
<211> LENGTH: 22
<212> TYPE: DNA
<213> ORGANISM: Artificial Sequence
<220> FEATURE:
<223> OTHER INFORMATION: Forward primer sequence for amplifying CCoAOMT

<400> SEQUENCE: 37
ctggctatgg atgtcaacag ag                                              22

<210> SEQ ID NO 38
<211> LENGTH: 22
<212> TYPE: DNA
<213> ORGANISM: Artificial Sequence
<220> FEATURE:
<223> OTHER INFORMATION: Reverse primer sequence for amplifying CCoAOMT

<400> SEQUENCE: 38
gttccatggt tcttctcgtc ag                                              22

<210> SEQ ID NO 39
<211> LENGTH: 22
<212> TYPE: DNA
<213> ORGANISM: Artificial Sequence
<220> FEATURE:
<223> OTHER INFORMATION: Forward primer sequence for amplifying 4CL

<400> SEQUENCE: 39
aggaaccttt tccggttaag tc                                              22

<210> SEQ ID NO 40
<211> LENGTH: 22
<212> TYPE: DNA
<213> ORGANISM: Artificial Sequence
<220> FEATURE:
<223> OTHER INFORMATION: Reverse primer sequence for amplifying 4CL

<400> SEQUENCE: 40
gatctggtga ccacgaatac aa                                              22

<210> SEQ ID NO 41
<211> LENGTH: 20
<212> TYPE: DNA
<213> ORGANISM: Artificial Sequence
<220> FEATURE:
<223> OTHER INFORMATION: Nad7pGER

<400> SEQUENCE: 41
ctatccacct ctccagacac                                                 20

<210> SEQ ID NO 42
<211> LENGTH: 20
<212> TYPE: DNA
<213> ORGANISM: Artificial Sequence
<220> FEATURE:
<223> OTHER INFORMATION: Nad7p1R

<400> SEQUENCE: 42
caaaaatttc acttcgaatt                                                 20

<210> SEQ ID NO 43
<211> LENGTH: 24
<212> TYPE: DNA
<213> ORGANISM: Artificial Sequence
<220> FEATURE:
<223> OTHER INFORMATION: RACEF1

<400> SEQUENCE: 43
atgacgacta ggaacgggca aatc                                           24

<210> SEQ ID NO 44
<211> LENGTH: 22
<212> TYPE: DNA
<213> ORGANISM: Artificial Sequence
<220> FEATURE:
<223> OTHER INFORMATION: RACE R1

<400> SEQUENCE: 44
gatcgaggaa attaagcagc tc                                             22

<210> SEQ ID NO 45
<211> LENGTH: 19
<212> TYPE: DNA
<213> ORGANISM: Artificial Sequence
<220> FEATURE:
<223> OTHER INFORMATION: RACE R2

<400> SEQUENCE: 45
cccgacagag agggaaaag                                                 19

<210> SEQ ID NO 46
<211> LENGTH: 402
<212> TYPE: DNA
<213> ORGANISM: Artificial Sequence
<220> FEATURE:
<223> OTHER INFORMATION: orf 133

<400> SEQUENCE: 46
atgcagttac tctttgagtt ggagtctctt ccggggtttt gctccagcct gtcccttaca    60
gatccagtag ttgcagttcc ccctttctg tcgtcggaaa gaggctctaa caagacctcg    120
aaccagcacc tctgggagaa aaagcgaact gcccttcgtt cttatcgtga caaaagttct    180
gttaggttct tagtagcaat cggcgaccct ttccttcttc tttccctttt ccctctctgt    240
cggggtcagg ggtgtcttcc ctttgctggc catcttggaa gaaatagttt aggaaggtca    300
gggatacgat ttgaatcccg agccccgata gccaatccga ataaagcggc agatctgcgg    360
actcaggaaa gaaagctttc agaaggtaag ttaagagcat ga                      402

<210> SEQ ID NO 47
<211> LENGTH: 96
<212> TYPE: DNA
<213> ORGANISM: Artificial Sequence
<220> FEATURE:
<223> OTHER INFORMATION: Synthetic Construct

<400> SEQUENCE: 47
atgacgacta ggaacgggca aatcaaaaac ctcaacatcc tgctgctcat gtatatacga    60
gaagttcggc ttatgcgatc aagtccgtaa agaccg                             96

<210> SEQ ID NO 48
<211> LENGTH: 88
<212> TYPE: DNA
<213> ORGANISM: Artificial Sequence
<220> FEATURE:

<223> OTHER INFORMATION: Synthetic Construct

<400> SEQUENCE: 48

```
atgacgacta ggaacgggta aatcaaaaac cccaacatcc tgctgctcat ggggcataaa      60
atagaagact ggttctattc tagatcct                                         88
```

<210> SEQ ID NO 49
<211> LENGTH: 1894
<212> TYPE: DNA
<213> ORGANISM: Artificial Sequence
<220> FEATURE:
<223> OTHER INFORMATION: Synthetic Construct

<400> SEQUENCE: 49

```
ataatcaccc gtaataggcg cagcggctgg cttttccagtt ttcggagttg aaagaatcgt      60
aagagaagta aacaggtttg attgcagtta tttcccgagt gggatagcat aagttgacca     120
agggacagac caaccttcta tttatatacg agtaagttcg gcttatgcga tcaagtccgt     180
aaagaccgaa agtgaagtgt atagaggaag tcagataact aggtatctga ccccacgcag     240
aagtatagtc agtcaagtcc gtaaaggctt cgtaagagga tgcccctcca aatccaagat     300
gcccgcctgg ggactcccgc atacccagt ggctgtagtt tatagtggtc tttcccagca      360
atctagttgc agttgcgtct ttccttcctt cgttaggacc agccgagtta gtataagtgc     420
cccattagaa gttccccgcc ggcagccaat tcccttgcga gcgtgccctt gaccagtggg     480
tgataattca tatgctgcgt tcgcgcgcta agccctttc ttcaaaattc cttacctgag      540
atgcagttac tctttgagtt ggagtctctt ccggggtttt gctccagcct gtcccttaca     600
gatccagtag ttgcagttcc ccctttctg tcgtcggaaa gaggctctaa caagacctcg      660
aaccagcacc tctgggagaa aaagcgaact gcccttcgtt cttatcgtga caaagttct     720
gttaggttct tagtagcaat cggcgacctt tccttcttc tttcccttttt ccctctctgt      780
cggggtcagg ggtgtcttcc ctttgctggc catcttggaa gaaatagttt aggaaggtca     840
gggatacgat ttgaatcccg agccccgata gccaatccga ataaagcggc agatctgcgg     900
actcaggaaa gaaagctttc agaaggtaag ttaagagcat gaaatagaaa agaggagta      960
tttggatgcc ctctctattc ttcgttataa gtatttcgga caagggcatt ttaatccttt    1020
tggatttcaa aatgataacc caagtgaaaa taacattgga aaaaaagata agagaggagg    1080
ccgctaaaat aaagttaaag tgaatgagta tttactttag accgtagtct aaataaataa    1140
gattaaataa agaaataata aaaatgaagg gcataaaata gaagactggt tctattctag    1200
atccttcttc agatctaggt tcatttttttt catcatatgt cagttttttgt ttttttcttt    1260
aagaatgcat ctggttctat cttttttttcc ggtatgccgc tccgccagca aggagcgaaa    1320
actaaaagca aacaaagata agatgaccag agagatcaag ctatatgtgg ataccacccc    1380
tagtgatttg gattttatga tgaatagtga tacggatttg cagtccttgt cttccccgga    1440
ttcgtccgac gcacagagtg cttcaccgga cttggaccta ttatgggatc aagtttgtgg    1500
tgaataccac aagtgtgtgc atgaatccgg gagggtctta cccccggaat ggacgatgcc    1560
cgaccttgtt cgggctgtta tttccgacga tgaagctatt gagcagggct ttctgacgga    1620
tgcctactat gatgtcatgt tatgtggcac tcatagttgg gtatgcgagg agctgcttaa    1680
tttcctcgat ctaatccact atggctgaga tgggtggaag gcggcacgcc aggtcgagct    1740
atcgctaagg tcgaaggaga tgcatttctg gtactggaca agctcttagg gaataatcta    1800
tttcttattt cttccttttt tcccatgacg actaggaacg ggcaaatcaa aaatttcact    1860
```

```
ttgaatttcg gacctcaaca tcctgctgct catg                            1894

<210> SEQ ID NO 50
<211> LENGTH: 1361
<212> TYPE: DNA
<213> ORGANISM: Artificial Sequence
<220> FEATURE:
<223> OTHER INFORMATION: Synthetic Construct

<400> SEQUENCE: 50
atgcagttac tctttgagtt ggagtctctt ccggggtttt gctccagcct gtcccttaca      60
gatccagtag ttgcagttcc ccctttctg tcgtcggaaa gaggctctaa caagacctcg     120
aaccagcacc tctgggagaa aaagcgaact gcccttcgtt cttatcgtga caaaagttct    180
gttaggttct tagtagcaat cggcgacctt ttccttcttc tttccttttt ccctctctgt    240
cggggtcagg ggtgtcttcc ctttgctggc catcttggaa gaaatagttt aggaaggtca    300
ggcatacgat ttgaatcccg agccccgata gccaatccga ataaagcggc agagcagcgg    360
actcaggaat caattctttc agaaggtaag ttaagagcat gaaatagaaa agaggagta     420 tttggatgcc ctctctattc ttcgttataa gtatttcgga caaggcatt ttaatcctt      480 tggatttcaa aatgataacc caagtgaaaa taacattgga aaaaaagata agagaggagg    540
ccgctaaaat aaagttaaag tgaatgagta tttactttag accgtagtct aaataaataa    600
gattaaataa agaaataata aaaatgaagg gcataaaata gaagactggt tctattctag    660
atccttcttc agatctagat tcatttttt catcatatgt cagttttgt tttttctttt      720 aagaatgcat ctggttctat cttttttcc ggtatgccgc tccgccagca aggagcgaaa     780
actagaagca aacaaagata agatgaccag agagatcaag ctatatgtgg acaccacccc    840
tagtgatttg gatttatga tgaatagtga tacggatttg cagtccttgt cttccccgga     900
ttcgtccgac gcacagagtg cttcaccgga cttggaccta ttatgggatc aagtttgtgg    960
tgaataccac aagtgtgtgc atgaagccgg gagggtctta ccccccggaat ggacgatgcc   1020 cgaccttgtt cggcaatct ttggcgatca agctattgag ctgggctttc tgacggatgc    1080
ctactatgat gtcatgttat gtggcactca tagttgggta tgcgaggagc tgcttaattt    1140
cctcgatcta atccactatg ttttttagtg gctgagatgg gtggaaggcg gcacgccagg   1200
tcgagctatc gctaaggtcg aaggagatgc atttctggta ctggacaagc tcttagggaa   1260
taatctattt cttatttctt cctttttcc catgacgact aggaacgggc aaatcaaaaa     1320
tttcactttg aatttcggac ctcaacatcc tgctgctcat g                       1361

<210> SEQ ID NO 51
<211> LENGTH: 55
<212> TYPE: DNA
<213> ORGANISM: Artificial Sequence
<220> FEATURE:
<223> OTHER INFORMATION: Synthetic Construct

<400> SEQUENCE: 51 ttttttctt taagaatgca tctggttcta tcttttttc cggtatgccg ctccg             55
```

CYTOPLASMIC MALE STERILITY GENE ORF147 OF PIGEONPEA, AND USES THEREOF

CROSS REFERENCE TO RELATED APPLICATIONS

This application is a national stage application under 35 U.S.C. § 371 of International Application No. PCT/IN2017/050564, filed internationally on Dec. 1, 2017, which claims priority to and the benefit of Indian Application No. 201641041375, filed on Dec. 2, 2016, the disclosures of each of which are herein incorporated by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 586862000700SUBSEQLIST.TXT, date recorded: Jan. 27, 2020, size: 21 KB).

FIELD OF INVENTION

The present disclosure relates to the field of plant biology and plant breeding. In particular, the disclosure provides an isolated polynucleotide fragment (cDNA) specific to pigeonpea that encodes a polypeptide, expression of which in mitochondria in floral specific manner results in male sterility.

BACKGROUND OF THE INVENTION

The cytoplasmic male sterility (CMS) phenotype is an outcome of incompatible interactions between the mitochondrial and nuclear genomes. The plant mitochondrial genome constitutes many sequences that actively recombine among themselves either by dividing into sub-genomic molecules or by joining with other molecules to form new ones. These recombination processes in mitochondrial genomes may create new molecular structures and novel open reading frames (ORFs), including CMS genes (Mackenzie et al., Plant Cell, 1999, 11, 571-585).

Several mutations are associated with the CMS trait. They include, the T-urf13 gene in *Zea mays* (Dewey et al. Cell, 1986, 44, 439-449), pcf gene in *Petunia* (Young et al., Cell, 1987, 50, 41-49), cox1 in *Oryza sativa* (Wang et al. Plant Cell, 2006, 18, 676-687) and mutations in ATPase subunits in *Helianthus annuus* (Laver et al., Plant J., 1991, 1, 185-193) and *Brassica napus* (Landgren et al., Plant Mol. Bio., 1996, 32, 879-890). The distinct variability in size and the multipartite structures of plant mitochondrial genomes make it difficult to study the physiological mechanism of CMS (Hanson et al., Plant Cell, 2004, 16, S154-169).

Pigeonpea [*Cajanus cajan* (L.) Millsp.] is an important high protein (20-22%) food legume of the rainfed tropics and sub-tropics of Asia, Africa and South America, cultivated by smallholder farmers. While the self-pollinating nature of legumes is a major bottleneck in exploiting hybrid vigor in these crops, pigeonpea has a unique advantage of being partially out-crossed (20 to 50%). Exploiting this, pigeonpea hybrid technology with $A_4$ (*C. cajanifolius*) cytoplasm involving a three-parent system is considered one of the breakthrough technological interventions in pulse breeding. This male sterile source designated as ICPA 2039, has been transferred into a number of genetic backgrounds and is highly stable across environments (Saxena et al. Euphytica, 2005, 145, 289-294; Saxena et al., J. Hered., 2010, 101, 497-503), however, the source of male sterility remains unknown, which remains a limitation in development of newer hybrid pigeonpea varieties for enhanced yield and quality. Elucidation can also potentially open the window for application and development of CMS lines in other pulses also.

SUMMARY OF THE INVENTION

In an aspect of the present disclosure, there is provided a DNA construct comprising a polynucleotide fragment, said polynucleotide fragment comprising a first, and a second sequence, wherein said first sequence encodes a mitochondrial transit peptide, said second sequence encodes a polypeptide having amino acid sequence as set forth in SEQ ID NO: 1, and said polynucleotide fragment is operably linked to a flower specific promoter.

In an aspect of the present disclosure, there is provided a DNA vector comprising a DNA construct, said DNA construct comprising a polynucleotide fragment, said polynucleotide fragment comprising a first, and a second sequence, wherein said first sequence encodes a mitochondrial transit peptide, said second sequence encodes a polypeptide having amino acid sequence as set forth in SEQ ID NO: 1, and said polynucleotide fragment is operably linked to a promoter that drives the expression to floral organs.

In an aspect of the present disclosure, there is provided a recombinant host cell comprising a DNA construct or a DNA vector comprising said DNA construct, said DNA construct comprising a polynucleotide fragment, said polynucleotide fragment comprising a first, and a second sequence, wherein said first sequence encodes a mitochondrial transit peptide, said second sequence encodes a polypeptide having amino acid sequence as set forth in SEQ ID NO: 1, and said polynucleotide fragment is operably linked to promoter that drives the expression to floral organs.

In an aspect of the present disclosure, there is provided a male sterile plant harboring in its genome a DNA construct, said DNA construct comprising a polynucleotide fragment, said polynucleotide fragment comprising a first, and a second sequence, wherein said first sequence encodes a mitochondrial transit peptide, said second sequence encodes a polypeptide having amino acid sequence as set forth in SEQ ID NO: 1, and said polynucleotide fragment is operably linked to a promoter that drives the expression to floral organs.

In an aspect of the present disclosure, there is provided a method of obtaining a male sterile plant harboring in its genome a DNA construct, said DNA construct comprising a polynucleotide fragment, said polynucleotide fragment comprising a first, and a second sequence, wherein said first sequence encodes a mitochondrial transit peptide, said second sequence encodes a polypeptide having amino acid sequence as set forth in SEQ ID NO: 1, and said polynucleotide fragment is operably linked to promoter that drives the expression to floral organs, said method comprising: (a) obtaining a DNA construct comprising a polynucleotide fragment, said polynucleotide fragment comprising a first, and a second sequence, wherein said first sequence encodes a mitochondrial transit peptide, said second sequence encodes a polypeptide having amino acid sequence as set forth in SEQ ID NO: 1, and said polynucleotide fragment is operably linked to promoter that drives the expression to floral organs from the group consisting AP3 promoter for floral expression from *Arabidopsis* (U30729), AP3 promoter for floral expression from Tomato (DQ539418.1), AP3 Promoter from *Coffea Arabica* (AHW58030.1), TA29 Promoter for Tapetum-specific expression from *Lycopersicon esculentum* (AM261325.1), and TA29 Promoter from Tobacco for Tapetum-specific expression (X52283) or a recombinant host cell comprising a DNA vector comprising said DNA construct; (b) transforming plant cells with said DNA construct or recombinant host cell; and (c) selecting and developing a transgenic plant capable of heterologously expressing a polypeptide having amino acid sequence as set forth in SEQ ID NO: 6, wherein said plant a male sterile plant.

In an aspect of the present disclosure, there is provided a method of identification of transgenic male sterile plants, said method comprising: (a) obtaining a transgenic plant biological material comprising DNA; (b) carrying out an amplification reaction using primers which bind to a DNA sequence as set forth in SEQ ID NO: 7 to generate amplicons; and (c) detecting the presence of said amplicons, wherein presence of said amplicons is indicative of the transgenic plant being male sterile.

In an aspect of the present disclosure, there is provided an isolated polynucleotide fragment comprising a first, and a second sequence, wherein the first sequence encodes a mitochondrial transit peptide, and said second sequence encodes a polypeptide having amino acid sequence as set forth in SEQ ID NO: 1.

These and other features, aspects, and advantages of the present subject matter will be better understood with reference to the following description and appended claims. This summary is provided to introduce a selection of concepts in a simplified form. This summary is not intended to identify key features or essential features of the claimed subject matter, nor is it intended to be used to limit the scope of the claimed subject matter.

BRIEF DESCRIPTION OF THE ACCOMPANYING DRAWINGS

The following drawings form part of the present specification and are included to further illustrate aspects of the present disclosure. The disclosure may be better understood by reference to the drawings in combination with the detailed description of the specific embodiments presented herein.

Figure 3A:
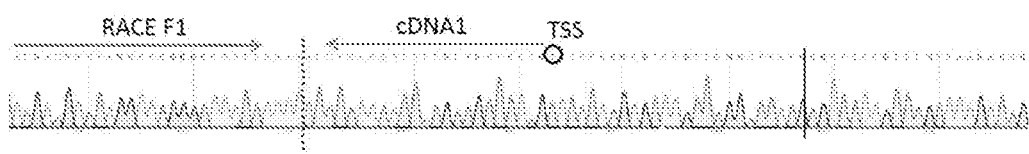
Figure 3B:
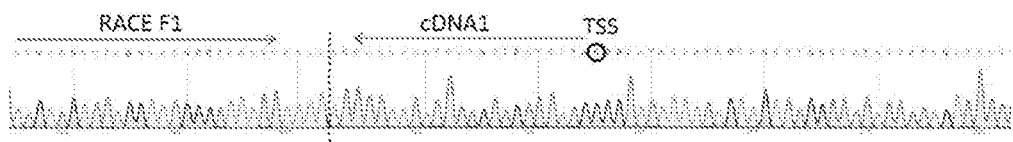

FIG. 3A, B depicts the DNA sequencing profile used to identify the transcription start sites (TSSs) in pigeonpea male sterile line, in accordance with an embodiment of the present disclosure. SEQ ID NO: 47 is shown in FIG. 3A; SEQ ID NO: 48 is shown in FIG. 3B.

Figure 3C:
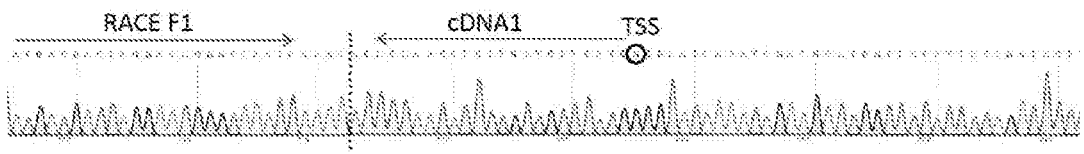

FIG. 3C depicts the DNA sequencing profile used to identify the transcription start sites (TSSs) in pigeonpea maintainer fertile line, in accordance with an embodiment of the present disclosure. SEQ ID NO: 48 is shown.

Figure 3D:
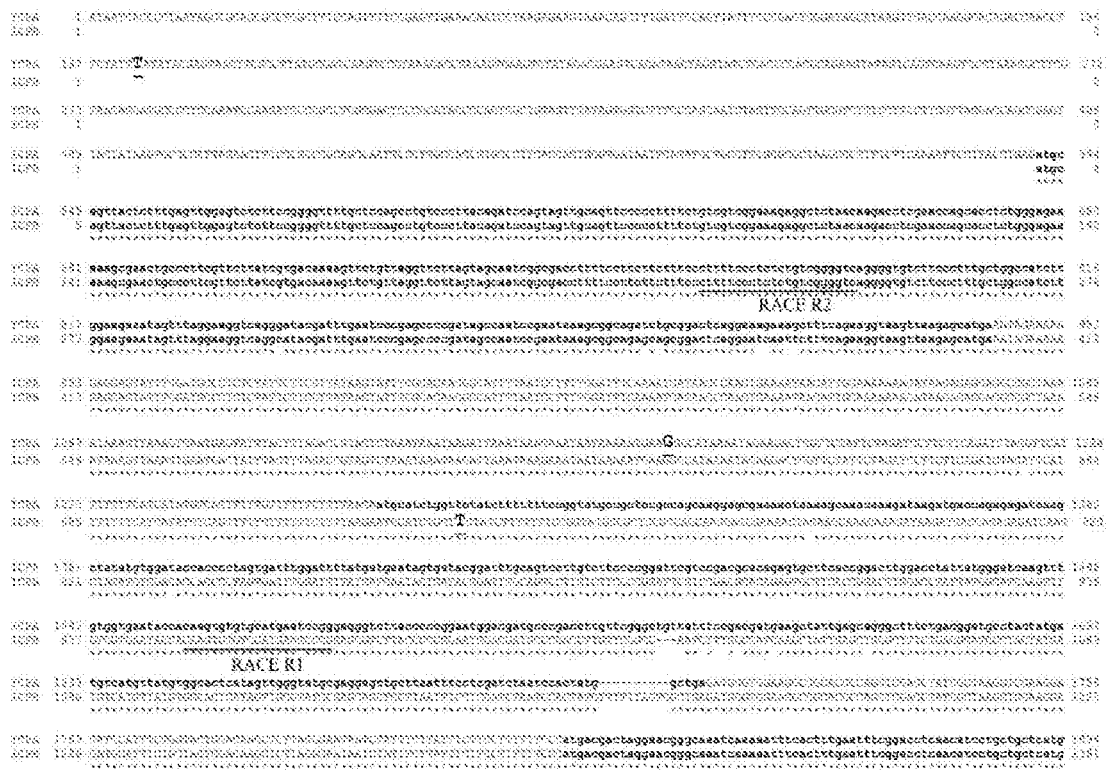

FIG. 3D depicts the comparison of nucleotide sequences of the 5' flanking region of nad7 in male fertile (upper) and CMS (lower) lines, in accordance with an embodiment of the present disclosure. SEQ ID NO: 49 is the top sequence and SEQ ID NO: 50 is the bottom sequence in the alignment.

FIG. 4A depicts the Secondary structure of the transcript predicted from ORF147 from the male sterile line using Sfold 2.2 software, in accordance with an embodiment of the present disclosure. SEQ ID NO: 51 is shown.

FIG. 4B depicts the predicted amino acid sequence of ORF147, in accordance with an embodiment of the present disclosure. SEQ ID NO: 1 is shown.

FIG. 5A depicts the effect of expression of orf147 on *E. coli* growth, in accordance with an embodiment of the present disclosure.

Figure 5B:
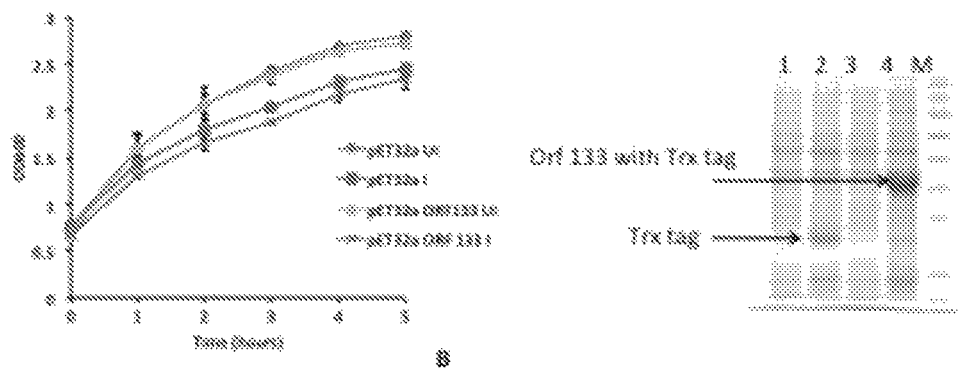

FIG. 5B depicts the effect of expression of orf133 on *E. coli* growth, in accordance with an embodiment of the present disclosure.

Figure 5C:
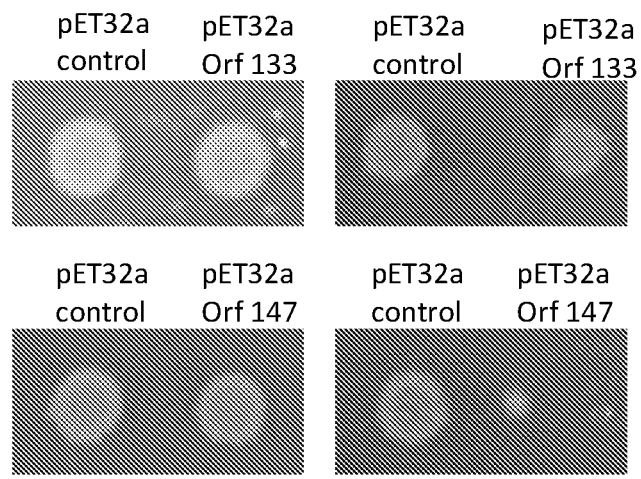

FIG. 5C depicts the bacterial growth upon expression of orf147 or orf133, in accordance with an embodiment of the present disclosure.

Figure 6A:
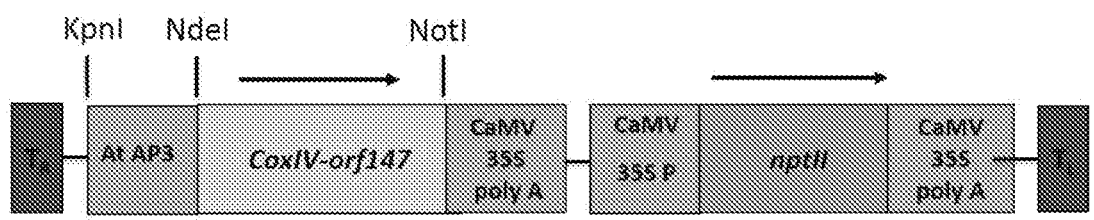

FIG. 6A depicts the schematic representation of T-DNA region of a plant transformation vector carrying the candidate cytoplasmic male sterility gene causing mitochondrial orf147 isolated from CMS pigeonpea line and fused with a yeast mitochondrial targeted peptide (CoxIV), cloned under the AP3 promoter from *Arabidopsis thaliana*, in accordance with an embodiment of the present disclosure.

FIG. 6B depicts the male sterile transgenic *Arabidopsis* plant showing normal growth and development, in accordance with an embodiment of the present disclosure.

FIG. 6C depicts the wild type plant with primary branches showing normal siliques, in accordance with an embodiment of the present disclosure.

FIG. 6D depicts the male sterile transgenic plant with short siliques indicating no developing seeds in accordance with an embodiment of the present disclosure.

FIG. 6E depicts the front view of normal mature flowers of WT (inset shows normal anther dehiscence), in accordance with an embodiment of the present disclosure.

FIG. 6F depicts the flowers of male sterile line revealing fused carpels, protruding pistil and short filaments (inset non-dehiscent anther in the transgenic flower), in accordance with an embodiment of the present disclosure.

FIG. 6G depicts the flower size, color and structure in the WT tobacco plant, in accordance with an embodiment of the present disclosure.

FIG. 6H depicts the flowers of male sterile tobacco plants having anthers below the stigma, in accordance with an embodiment of the present disclosure.

FIG. 6I depicts the seed capsules from *N. tabacum* (WT) (top), and that of sterile progeny (bottom), in accordance with an embodiment of the present disclosure.

FIG. 6J depicts the seed capsules of WT plants (Left), collapsed and detached seed capsules in partially sterile transgenic phenotypes (Inset) floral branches from wild type (WT), in accordance with an embodiment of the present disclosure.

Figure 7A:
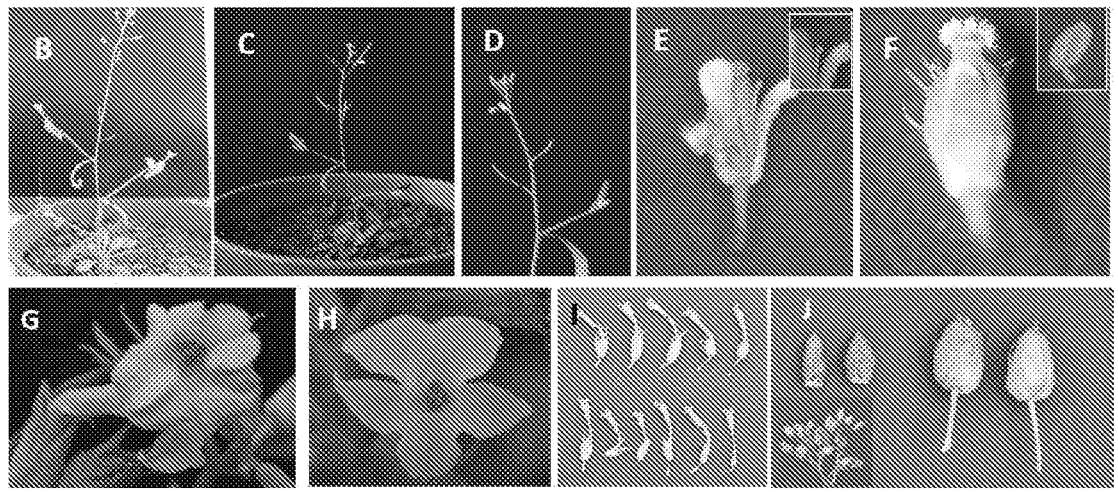

FIG. 7A depicts the expression of mitochondrial orf147 in pigeonpea male sterile plant (ICPA 2039) vs. pigeonpea maintainer line (ICPB 2039), in accordance with an embodiment of the present disclosure.

Figure 7A:
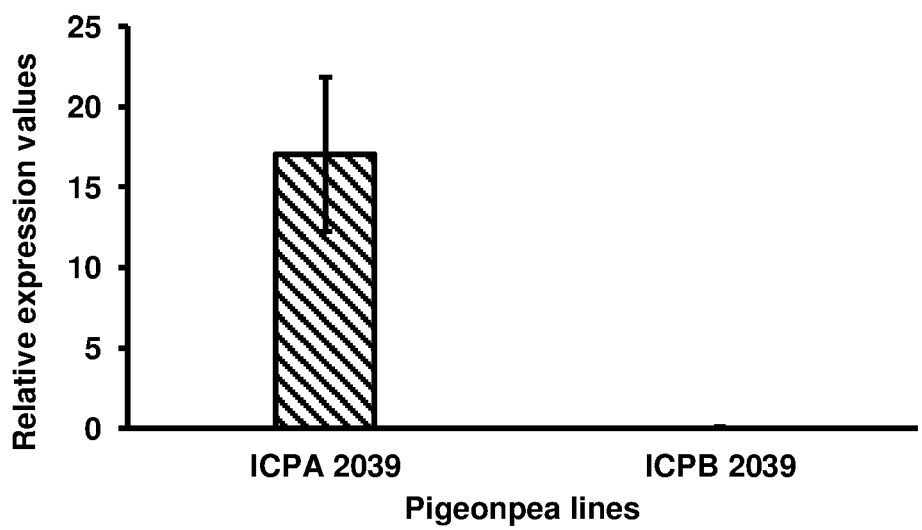
Figure 7B:
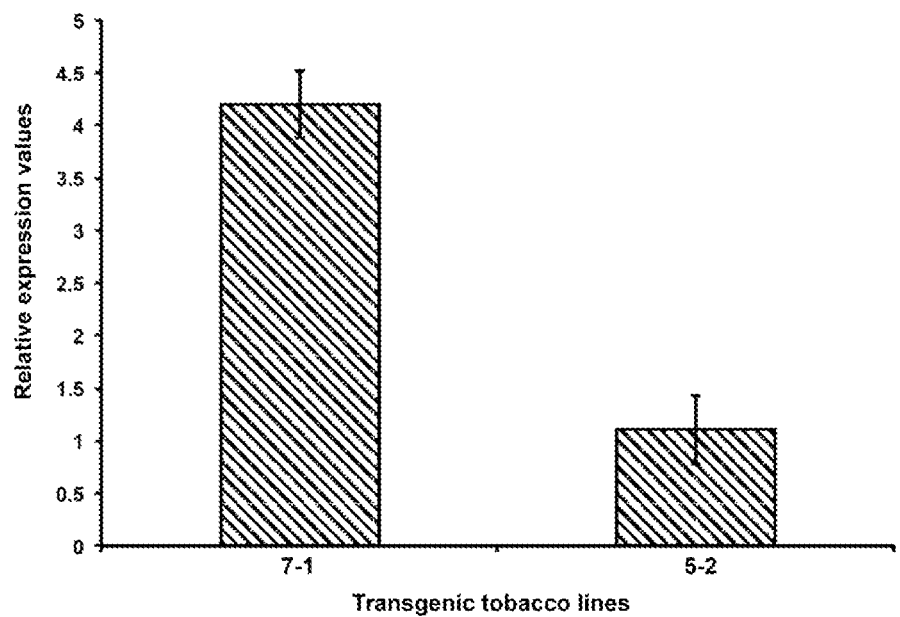

FIG. 7B depicts the expression of mitochondrial orf147 in completely sterile transgenic *Arabidopsis* (left), and partially sterile transgenic tobacco (right), in a accordance with an embodiment of the present disclosure.

Figure 8A:
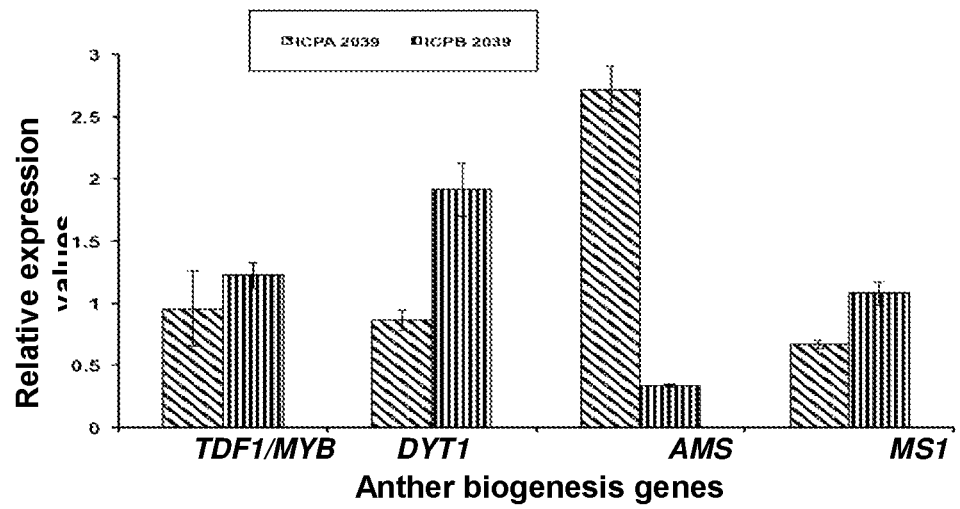

FIG. 8A depicts the real-time qRT-PCR showing reduced gene expression of TDF1, DYT and MS1 in flower buds of the male sterile pigeonpea line (ICPA 2039) compared to those of the fertile maintainer line (ICPB 2039), in accordance with an embodiment of the present disclosure.

FIG. 8B depicts the male sterile transgenic *Arabidopsis* showing decreased expressions of key genes DYT1, AMS and MS1, in accordance with an embodiment of the present disclosure.

FIG. 9A depicts the phloroglucinol stained anthers in a bunch of flowers of wild type *Arabidopsis* plant, in accordance with an embodiment of the present disclosure.

FIG. 9B depicts the close up view of deeply stained (phloroglucinol) WT *Arabidopsis* anther, in accordance with an embodiment of the present disclosure.

FIG. 9C depicts the anthers of a male sterile transgenic plant with reduced staining (phloroglucinol) indicating reduced lignification (inset), in accordance with an embodiment of the present disclosure.

FIG. 9D depicts the WT transgenic tobacco anthers accumulating stain (phloroglucinol), in accordance with an embodiment of the present disclosure.

FIG. 9E depicts the anthers of partially sterile tobacco transgenic plant, in accordance with an embodiment of the present disclosure.

FIG. 9F depicts the anthers of fully sterile male plant accumulating very little stain (phloroglucinol), in accordance with an embodiment of the present disclosure.

Figure 9G:
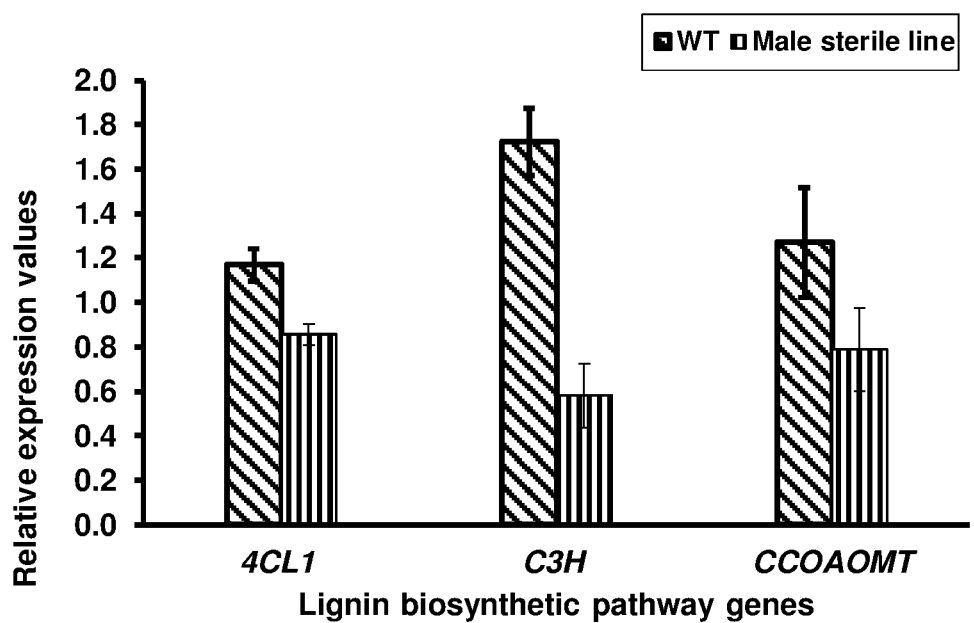

FIG. 9G depicts the reduced relative gene expression of lignin biosynthesis genes such as 4CL (4 Coumarate:CoAligase), CCoAOMT (Caffeoyl CoA O-methyltransferase), and C3H (Cinnamic acid 3-hydroxylase) in male sterile transgenic *Arabidopsis* plants, in accordance with an embodiment of the present disclosure.

DETAILED DESCRIPTION OF THE INVENTION

Those skilled in the art will be aware that the present disclosure is subject to variations and modifications other than those specifically described. It is to be understood that the present disclosure includes all such variations and modifications. The disclosure also includes all such steps, features, compositions and compounds referred to or indicated in this specification, individually or collectively, and any and all combinations of any or more of such steps or features.

Definitions

For convenience, before further description of the present disclosure, certain terms employed in the specification, and examples are collected here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

The terms "comprise" and "comprising" are used in the inclusive, open sense, meaning that additional elements may be included. It is not intended to be construed as "consists of only".

Throughout this specification, unless the context requires otherwise the word "comprise", and variations such as "comprises" and "comprising", will be understood to imply the inclusion of a stated element or step or group of element or steps but not the exclusion of any other element or step or group of element or steps.

The term "including" is used to mean "including but not limited to". "Including" and "including but not limited to" are used interchangeably.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the disclosure, the preferred methods, and materials are now described. All publications mentioned herein are incorporated herein by reference. The present disclosure is not to be limited in scope by the specific embodiments described herein, which are intended for the purposes of exemplification only. Functionally-equivalent products, compositions, and methods are clearly within the scope of the disclosure, as described herein.

Sequences:

SEQ ID NO: 1 depicts the amino acid sequence of polypeptide encoded by orf147.

```
MHLVLSFFPVCRSASKERKLKANKDKMTREIKLYVDTTPSDLDFMMNSDT
DLQSLSSPDSSDAQSASPDLDLLWDQVCGEYHKCVHESGRVLPPEWTMPD
LVRAVISDDEAIEQGFLTDAYYDVMLCGTHSWVCEELLNFLDLIHYG
```

SEQ ID NO: 2 depicts the mitochondrial transit peptide amino acid sequence.

```
MLSLRQSIRFFKPATRTLCSSRYLLQQKP
```

SEQ ID NO: 3 depicts the nucleotide sequence of orf147.

```
ATGCATCTGGTTCTATCTTTTTTTCCGGTATGCCGCTCCGCCAGCAAGGA
GCGAAAACTAAAAGCAAACAAAGATAAGATGACCAGAGAGATCAAGCTAT
ATGTGGATACCACCCCTAGTGATTTGGATTTTATGATGAATAGTGATACG
GATTTGCAGTCCTTGTCTTCCCCGGATTCGTCCGACGCACAGAGTGCTTC
ACCGGACTTGGACCTATTATGGGATCAAGTTTGTGGTGAATACCACAAGT
GTGTGCATGAATCCGGGAGGGTCTTACCCCCGGAATGGACGATGCCCGAC
CTTGTTCGGGCTGTTATTTCCGACGATGAAGCTATTGAGCAGGGCTTTCT
GACGGATGCCTACTATGATGTCATGTTATGTGGCACTCATAGTTGGGTAT
GCGAGGAGCTGCTTAATTTCCTCGATCTAATCCACTATGGCTGA
```

SEQ ID NO: 4 depicts the nucleotide sequence encoding mitochondrial transit peptide.

```
ATGTTGTCACTACGTCAATCTATAAGATTTTTCAAGCCAGCCACAAGAAC
TTTGTGTAGCTCTAGATATCTGCTTCAGCAAAAACCC
```

SEQ ID NO: 5 depicts the *Arabidopsis* promoter sequence.

CAGTAACTGTGGCCAACTTAGTTTTGAAACAACACTAACTGGTCGAAGCAA
AAAGAAAAAGAGTTTCATCATATATCTGATTTGATGGACTGTTTGGAGTT
AGGACCAAACATTATCTACAAACAAAGACTTTTCTCCTAACTTGTGATTCC
TTCTTAAACCCTAGGGGTAATATTCTATTTTCCAAGGATCTTTAGTTAAAG
GCAAATCCGGGAAATTATTGTAATCATTTGGGGAAACATATAAAAGATTTG
AGTTAGATGGAAGTGACGATTAATCCAAACATATATATCTCTTTCTTCTTA
TTTCCCAAATTAACAGACAAAAGTAGAATATTGGCTTTTAACACCAATATA
AAAACTTGTTCACACCTAAACACTTTTGTTTACTTTAGGGTAAGTGTAAAA
AGCCAACCAAATCCACCTGCACTGATTTGACGTTTACAAACGCCGTTAAGT
TTGTCACCGTCTAAACAAAAACAAAGTAGAAGCTAACGGAGCTCCGTTAAT
AAATTGACGAAAAGCAAACCAAGTTTTTAGCTTTGGTCCCCCTCTTTTACC
AAGTGACAATTGATTTAAGCAGTGTCTTGTAATTATACAACCATCGATGTC
CGTTGATTTAAACAGTGTCTTGTAATTAAAAAAATCAGTTTACATAAATGG
AAAATTTATCACTTAGTTTTCATCAACTTCTGAACTTACCTTTCATGGATT
AGGCAATACTTTCCATTTTTAGTAACTCAAGTGGACCCTTTACTTCTTCAA
CTCCATCTCTCTCTTTCTATTTCACTTCTTTCTTCTCATTATATCTCTTGT
CCTCTCCACCAAATCTCTTCAACAAAAAGATTAAACAAAGAGAGAAGAATC
AT

SEQ ID NO: 6 depicts the amino acid sequence of a polypeptide comprising mitochondrial transit peptide fused to Orf147.

MLSLRQSIRFFKPATRTLCSSRYLLQQKPMHLVLSFFPVCRSASKERKLKA
NKDKMTREIKLYVDTTPSDLDFMMNSDTDLQSLSFPDSSDAQSASPDLDLL
WDRVCGEYHKCVHESGRVLPPEWTMPDLVRAVISDDEAIEQGFLTDAYYDV
MLCGTHSWVCEELLNFLDLIHYG

SEQ ID NO: 7 depicts the nucleotide sequence of a polynucleotide fragment encoding a mitochondrial transit peptide fused to orf147.

ATGTTGTCACTACGTCAATCTATAAGATTTTTCAAGCCAGCCACAAGAAC
TTTGTGTAGCTCTAGATATCTGCTTCAGCAAAAACCCATGCATCTGGTTC
TATCTTTTTTTCCGGTATGCCGCTCCGCCAGCAAGGAGCGAAAACTAAAA
GCAAACAAGATAAGATGACCAGAGAGATCAAGCTATATGTGGATACCAC
CCCTAGTGATTTGGATTTTATGATGAATAGTGATACGGATTTGCAGTCCT
TGTCTTTCCCGGATTCGTCTGACGCACAGAGTGCTTCACCGGACTTGGAC
CTATTATGGGATCGAGTTTGTGGTGAATACCACAAGTGTGTGCATGAATC
CGGGAGGGTCTTACCCCCGGAATGGACGATGCCCGACCTTGTTCGGGCTG
TTATTTCCGACGATGAAGCTATTGAGCAGGGCTTTCTGACGGATGCCTAC
TATGATGTCATGTTATGTGGCACTCATAGTTGGGTATGCGAGGAGCTGCT
TAATTTCCTCGATCTAATCCACTATGGCTGA

SEQ ID NO: 8 depicts the antisense primer sequence used for PCR based directional genome walking.

AATTCAAAGTGAAATTTTTG

SEQ ID NO: 9 depicts the forward primer sequence for amplifying orf133.

ATGCAGTTACTCTTTGAGTTGGA

SEQ ID NO: 10 depicts the reverse primer sequence for amplifying orf133.

TCATGCTCTTAACTTACCTTCTG

SEQ ID NO: 11 depicts the forward primer sequence for amplifying orf147.

ATGCATCTGGTTCTATCTT

SEQ ID NO: 12 depicts the reverse primer sequence for amplifying orf147.

TCAGCCATAGTGGATTAGATCGAG

SEQ ID NO: 13 depicts the forward primer sequence with NdeI restriction site for orf133.

TCAGCCATAGTGGATTAGATCGAG

SEQ ID NO: 14 depicts the reverse primer sequence with SalI restriction site for orf133.

ATAGTCGACTCATGCTCTTAACTTACCTTCTG

SEQ ID NO: 15 depicts the forward primer sequence with NdeI restriction site for orf147.

TATCATATGCATCTGGTTCTATCTT

SEQ ID NO: 16 depicts the forward primer sequence with SalI restriction site for orf147.

TATGTCGACTCAGCCATAGTGGATTAGATCG

SEQ ID NO: 17 depicts the forward primer with KpnI site for amplifying AtAP3 promoter.

TAGGTACCCAGTAACTGTGGCCAACTTAGTT

SEQ ID NO: 18 depicts the reverse primer with NdeI site for amplifying AtAP3 promoter.

TCAGATCATATGATTCTTCTCTCTTTGTTTAATCT

SEQ ID NO: 19 depicts the forward primer for amplifying CoxIV mitochondrial signal peptide.

ATGTTGTCACTACGTCAATCTATAAG

SEQ ID NO: 20 depicts the reverse primer for amplifying CoxIV mitochondrial signal peptide.

GGGTTTTTGCTGAAGCAGAT

SEQ ID NO: 21 depicts the forward primer for amplifying CoxIV orf147 fusion.

ATCTGCTTCAGCAAAAACCCATGCATCTGGTTCTATCTTTTTTC

SEQ ID NO: 22 depicts the reverse primer for amplifying CoxIV orf147 fusion.

GAAAAAAGATAGAACCAGATGCATGGGTTTTTGCTGAAGCAGAT

SEQ ID NO: 23 depicts the forward primer with NdeI restriction site for amplifying CoxIV orf147 fusion.

TATCATATGTTGTCACTACGTCAATCTATAAG

SEQ ID NO: 24 depicts the reverse primer with NotI restriction site for amplifying CoxIV orf147 fusion.

GCGGCCGCTCAGCCATAGTGGATTAGATCG

SEQ ID NO: 25 depicts the forward primer sequence for amplifying DYT1.

GAAGCTCCTCCTGAGATTGATG

SEQ ID NO: 26 depicts the reverse primer sequence for amplifying DYT1.

CTTCCTCTCCCCAATCTTACAC

SEQ ID NO: 27 depicts the forward primer sequence for amplifying AMS.

AGGCTCTATGCAAAACGAAAAG

SEQ ID NO: 28 depicts the reverse primer sequence for amplifying AMS.

GGTTGTGGTAATGGTTGATGTG

SEQ ID NO: 29 depicts the forward primer sequence for amplifying SAND.

GTGCAGACACAAGGTTGTCAGT

SEQ ID NO: 30 depicts the reverse primer sequence for amplifying SAND.

GGTAGGCAGATTGGTGAGAAAG

SEQ ID NO: 31 depicts the forward primer sequence for amplifying TIP41.

GAAGATGAGGCACCAACTGTTC

SEQ ID NO: 32 depicts the reverse primer sequence for amplifying TIP41.

GCTTAATCACTGGAAGCCTCTG

SEQ ID NO: 33 depicts the forward primer sequence for amplifying UNK.

GCTGAGAAGCATGTTCAGGAGT

SEQ ID NP: 34 depicts the reverse primer sequence for amplifying UNK.

GTTCATGAGCTCAGAGAGACCA

SEQ ID NO: 35 depicts the forward primer sequence for amplifying C3H.

AGTTCGACAGAGTGGTTGGACT

SEQ ID NO: 36 depicts the reverse primer sequence for amplifying C3H.

GCTTCGGTGAGGTAGCATTAGA

SEQ ID NO: 37 depicts the forward primer sequence for amplifying CCoAOMT.

CTGGCTATGGATGTCAACAGAG

SEQ ID NO: 38 depicts the reverse primer sequence for amplifying CCoAOMT.

GTTCCATGGTTCTTCTCGTCAG

SEQ ID NO: 39 depicts the forward primer sequence for amplifying 4CL.

AGGAACCTTTTCCGGTTAAGTC

SEQ ID NO: 40 depicts the reverse primer sequence for amplifying 4CL.

GATCTGGTGACCACGAATACAA

SEQ ID NO: 41 depicts Nad7pGER:

CTATCCACCTCTCCAGACAC

SEQ ID NO: 42 depicts Nad7p1R:

CAAAAATTTCACTTCGAATT

SEQ ID NO: 43 depicts RACEF1:

ATGACGACTAGGAACGGGCAAATC

SEQ ID NO: 44 depicts RACE R1:

GATCGAGGAAATTAAGCAGCTC

SEQ ID NO: 45 depicts RACE R2:

CCCGACAGAGAGGGAAAAG

SEQ ID NO: 46 depicts orf 133

ATGCAGTTACTCTTTGAGTTGGAGTCTCTTCCGGGGTTTTGCTCCAGCCT
GTCCCTTACAGATCCAGTAGTTGCAGTTCCCCCTTTTCTGTCGTCGGAAA
GAGGCTCTAACAAGACCTCGAACCAGCACCTCTGGGAGAAAAAGCGAACT
GCCCTTCGTTCTTATCGTGACAAAAGTTCTGTTAGGTTCTTAGTAGCAAT
CGGCGACCTTTTCCTTCTTCTTTCCCTTTTCCCTCTCTGTCGGGGTCAGG
GGTGTCTTCCCTTTGCTGGCCATCTTGGAAGAAATAGTTTAGGAAGGTCA
GGGATACGATTTGAATCCCGAGCCCCGATAGCCAATCCGAATAAAGCGGC
AGATCTGCGGACTCAGGAAAGAAAGCTTTCAGAAGGTAAGTTAAGAGCAT
GA

In an embodiment of the present disclosure, there is provided a DNA construct comprising a polynucleotide fragment, said polynucleotide fragment comprising a first, and a second sequence, wherein said first sequence encodes a mitochondrial transit peptide, said second sequence encodes a polypeptide having amino acid sequence as set forth in SEQ ID NO: 1, and said polynucleotide fragment is operably linked to promoter that drives the expression to floral organs. The floral promoter is selected from the group consisting of AP3 promoter for floral expression from *Arabidopsis* (U30729), AP3 promoter for floral expression from Tomato (DQ539418.1), AP3 Promoter from *Coffea Arabica* (AHW58030.1), TA29 Promoter for Tapetum-specific expression from *Lycopersicon esculentum* (AM261325.1), and TA29 Promoter from Tobacco for Tapetum-specific expression (X52283).

In an embodiment of the present disclosure, there is provided a DNA construct as described herein, wherein said second sequence is as set forth in SEQ ID NO: 3. In an embodiment of the present disclosure, there is provided a DNA construct as described herein, wherein said mitochondrial transit peptide is selected from the group consisting of mitochondrial transit peptide of the cytochrome oxidase subunit IV from yeast, and COX4 from *Saccharomyces cerevisiae* (P04037|1-25).

In an embodiment of the present disclosure, there is provided a DNA construct as described herein, wherein said mitochondrial transit peptide amino acid sequence is as set forth in SEQ ID NO: 2, and is fused in-frame at the 5' end of said second sequence.

In an embodiment of the present disclosure, there is provided a DNA construct as described herein, wherein said mitochondrial transit peptide amino acid sequence is as set forth in SEQ ID NO: 2, and is fused in-frame at the 5' end of SEQ ID NO: 1.

In an embodiment of the present disclosure, there is provided a DNA construct as described herein, wherein said first sequence is as set forth in SEQ ID NO: 4.

In an embodiment of the present disclosure, there is provided a DNA construct as described herein, wherein said flower specific promoter is selected from the group consisting of AP3 promoter for floral expression from *Arabidopsis* (U30729), AP3 promoter for floral expression from Tomato (DQ539418.1), AP3 Promoter from *Coffea Arabica* (AHW58030.1), TA29 Promoter for Tapetum-specific expression from *Lycopersicon esculentum* (AM261325.1), and TA29 Promoter from Tobacco for Tapetum-specific expression (X52283). The developmentally regulated APETALA3 promoter from *Arabidopsis thaliana* (AP3) which is specific to petals and stamens, (Jack, T. et al. (1994) Cell 76, 703-716) AP3 was chosen as a tissue specific promoter because it is expressed very early in the development of the stamen (as well as the petal).). A person skilled in the art can use any flower or anther specific promoter to drive the expression of orf147 fragment In an embodiment of the present disclosure, there is provided a DNA construct as described herein, wherein said flower specific promoter sequence is as set forth in SEQ ID NO: 5.

In an embodiment of the present disclosure, there is provided a DNA construct comprising a polynucleotide fragment, said polynucleotide fragment comprising a first, and a second sequence, wherein said first sequence encodes a mitochondrial transit peptide having amino acid sequence as set forth in SEQ ID NO: 2, and said second sequence encodes a polypeptide having amino acid sequence as set forth in SEQ ID NO: 1, and said polynucleotide fragment is operably linked to a flower specific promoter having sequence as set forth in SEQ ID NO: 5.

In an embodiment of the present disclosure, there is provided a DNA construct comprising a polynucleotide fragment, said polynucleotide fragment comprising a first, and a second sequence, wherein said first sequence encodes a mitochondrial transit peptide encoded by a sequence as set forth in SEQ ID NO: 4, and said second sequence is as set forth in SEQ ID NO: 3, and said polynucleotide fragment is operably linked to a flower specific promoter having sequence as set forth in SEQ ID NO: 5.

In an embodiment of the present disclosure, there is provided a DNA vector comprising a DNA construct, said DNA construct comprising a polynucleotide fragment, said polynucleotide fragment comprising a first, and a second sequence, wherein said first sequence encodes a mitochondrial transit peptide, said second sequence encodes a polypeptide having amino acid sequence as set forth in SEQ ID NO: 1, and said polynucleotide fragment is operably linked to a flower specific promoter.

In an embodiment of the present disclosure, there is provided a DNA vector as described herein, wherein said second sequence is as set forth in SEQ ID NO: 3.

In an embodiment of the present disclosure, there is provided a DNA vector as described herein, wherein said mitochondrial transit peptide is selected from the group consisting of mitochondrial transit peptide of the cytochrome oxidase subunit IV from yeast, and COX4 from *Saccharomyces cerevisiae* (P04037|1-25). A person skilled in the art can use any other mitochondrial transit peptide.

In an embodiment of the present disclosure, there is provided a DNA vector as described herein, wherein said mitochondrial transit peptide amino acid sequence is as set forth in SEQ ID NO: 2, and is fused in-frame at the 5' end of said second sequence.

In an embodiment of the present disclosure, there is provided a DNA vector as described herein, wherein said mitochondrial transit peptide amino acid sequence is as set forth in SEQ ID NO: 2, and is fused in-frame at the 5' end of SEQ ID NO: 1.

In an embodiment of the present disclosure, there is provided a DNA vector as described herein, wherein said first sequence is as set forth in SEQ ID NO: 4. In an embodiment of the present disclosure, there is provided a DNA vector as described herein, wherein said flower specific promoter is selected from the group consisting of AP3 promoter for floral expression from *Arabidopsis* (U30729), AP3 promoter for floral expression from Tomato (DQ539418.1), AP3 Promoter from *Coffea Arabica* (AHW58030.1), TA29 Promoter for Tapetum-specific expression from *Lycopersicon esculentum* (AM261325.1), and TA29 Promoter from Tobacco for Tapetum-specific expression (X52283). The developmentally regulated *APETALA*3 promoter from *Arabidopsis thaliana* (AP3) which is specific to petals and stamens, (Jack, T. et al. (1994) Cell 76, 703-716); AP3 was chosen as a tissue specific promoter because it is expressed very early in the development of the stamen (as well as the petal).

In an embodiment of the present disclosure, there is provided a DNA vector as described herein, wherein said anther specific promoter sequence is as set forth in SEQ ID NO: 5.

In an embodiment of the present disclosure, there is provided a DNA vector comprising a DNA construct, wherein said DNA construct comprises a polynucleotide fragment, said polynucleotide fragment comprising a first, and a second sequence, wherein said first sequence encodes a mitochondrial transit peptide having amino acid sequence as set forth in SEQ ID NO: 2, and said second sequence encodes a polypeptide having amino acid sequence as set forth in SEQ ID NO: 1, and said polynucleotide fragment is operably linked to a flower specific promoter having sequence as set forth in SEQ ID NO: 5.

In an embodiment of the present disclosure, there is provided a DNA vector comprising a DNA construct, wherein said DNA construct comprises a polynucleotide fragment, said polynucleotide fragment comprising a first, and a second sequence, wherein said first sequence encodes a mitochondrial transit peptide encoded by a sequence as set forth in SEQ ID NO: 4, and said second sequence as set forth in SEQ ID NO: 3, and said polynucleotide fragment is operably linked to a flower specific promoter having sequence as set forth in SEQ ID NO: 5.

In an embodiment of the present disclosure, there is provided a recombinant host cell comprising a DNA construct, said DNA construct comprising a polynucleotide fragment, said polynucleotide fragment comprising a first, and a second sequence, wherein said first sequence encodes a mitochondrial transit peptide, said second sequence encodes a polypeptide having amino acid sequence as set forth in SEQ ID NO: 1, and said polynucleotide fragment is operably linked to a flower specific promoter.

In an embodiment of the present disclosure, there is provided a recombinant host cell comprising a DNA construct as described herein, wherein said second sequence is as set forth in SEQ ID NO: 3.

In an embodiment of the present disclosure, there is provided a recombinant host cell comprising a DNA construct as described herein, wherein said mitochondrial transit peptide is selected from the group consisting of mitochondrial transit peptide of the cytochrome oxidase subunit IV from yeast, and COX4 from *Saccharomyces cerevisiae* (P04037|1-25).

In an embodiment of the present disclosure, there is provided a recombinant host cell comprising a DNA construct as described herein, wherein said mitochondrial transit peptide amino acid sequence is as set forth in SEQ ID NO: 2, and is fused in-frame at the 5' end of said second sequence.

In an embodiment of the present disclosure, there is provided a recombinant host cell comprising a DNA construct as described herein, wherein said mitochondrial transit peptide amino acid sequence is as set forth in SEQ ID NO: 2, and is fused in-frame at the 5' end of SEQ ID NO: 1.

In an embodiment of the present disclosure, there is provided a recombinant host cell comprising a DNA construct as described herein, wherein said first sequence is as set forth in SEQ ID NO: 4.

In an embodiment of the present disclosure, there is provided a recombinant host cell comprising a DNA construct as described herein, wherein said flower specific promoter is selected from the group consisting of AP3 promoter for floral expression from *Arabidopsis* (U30729), AP3 promoter for floral expression from Tomato (DQ539418.1), AP3 Promoter from *Coffea Arabica* (AHW58030.1), TA29 Promoter for Tapetum-specific expression from *Lycopersicon esculentum* (AM261325.1), and TA29 Promoter from Tobacco for Tapetum-specific expression (X52283). The developmentally regulated APETALA3 promoter from *Arabidopsis thaliana* (AP3) which is specific to petals and stamens, (Jack, T. et al. (1994) Cell 76, 703-716); AP3 was chosen as a tissue specific promoter because it is expressed very early in the development of the stamen (as well as the petal).

In an embodiment of the present disclosure, there is provided a recombinant host cell comprising a DNA construct as described herein, wherein said flower specific promoter sequence is as set forth in SEQ ID NO: 5.

In an embodiment of the present disclosure, there is provided a recombinant host cell comprising a DNA construct, said DNA construct comprising a polynucleotide fragment, said polynucleotide fragment comprising a first, and a second sequence, wherein said first sequence encodes a mitochondrial transit peptide having amino acid sequence as set forth in SEQ ID NO: 2, and said second sequence encodes a polypeptide having amino acid sequence as set forth in SEQ ID NO: 1, and said polynucleotide fragment is operably linked to a flower specific promoter having sequence as set forth in SEQ ID NO: 5.

In an embodiment of the present disclosure, there is provided a recombinant host cell comprising a DNA construct, said DNA construct comprising a polynucleotide fragment, said polynucleotide fragment comprising a first, and a second sequence, wherein said first sequence encodes a mitochondrial transit peptide encoded by a sequence as set forth in SEQ ID NO: 4, and said second sequence as set forth in SEQ ID NO: 3, and said polynucleotide fragment is operably linked to a flower specific promoter having sequence as set forth in SEQ ID NO: 5.

In an embodiment of the present disclosure, there is provided a recombinant host cell comprising a DNA construct as described herein, wherein said recombinant host cell is a plant cell.

In an embodiment of the present disclosure, there is provided a recombinant host cell comprising a DNA construct as described herein, wherein said recombinant host cell is a monocot.

In an embodiment of the present disclosure, there is provided a recombinant host cell comprising a DNA construct as described herein, wherein said recombinant host cell is a dicot.

In an embodiment of the present disclosure, there is provided a recombinant host cell comprising a DNA construct as described herein, wherein said recombinant host cell is selected from the group consisting of kidney bean, lima bean, mung bean, black gram, broad bean, field bean, garden pea, chick pea, black eyed pea, pigeonpea, tobacco, rice, maize, wheat, sorghum, and lentil.

In an embodiment of the present disclosure, there is provided a recombinant host cell comprising a DNA construct as described herein, wherein said recombinant host cell is tobacco or *Arabidopsis*.

In an embodiment of the present disclosure, there is provided a recombinant host cell comprising a DNA construct as described herein, wherein said recombinant host cell is pigeonpea or lentil.

In an embodiment of the present disclosure, there is provided a recombinant host cell comprising a DNA vector, said DNA vector comprising a DNA construct, said DAN construct comprising a polynucleotide fragment, said polynucleotide fragment comprising a first, and a second sequence, wherein said first sequence encodes a mitochondrial transit peptide, said second sequence encodes a polypeptide having amino acid sequence as set forth in SEQ ID NO: 1, and said polynucleotide fragment is operably linked to a flower specific promoter.

In an embodiment of the present disclosure, there is provided a recombinant host cell comprising a DNA vector as described herein, wherein said second sequence is as set forth in SEQ ID NO: 3.

In an embodiment of the present disclosure, there is provided a recombinant host cell comprising a DNA vector as described herein, wherein said mitochondrial transit peptide is selected from the group consisting of mitochondrial transit peptide of the cytochrome oxidase subunit IV from yeast, and COX4 from *Saccharomyces cerevisiae* (P04037|1-25).

In an embodiment of the present disclosure, there is provided a recombinant host cell comprising a DNA vector as described herein, wherein said mitochondrial transit peptide amino acid sequence is as set forth in SEQ ID NO: 2, and is fused in-frame at the 5' end of said second sequence.

In an embodiment of the present disclosure, there is provided a recombinant host cell comprising a DNA vector as described herein, wherein said mitochondrial transit peptide amino acid sequence is as set forth in SEQ ID NO: 2, and is fused in-frame at the 5' end of SEQ ID NO: 1.

In an embodiment of the present disclosure, there is provided a recombinant host cell comprising a DNA vector as described herein, wherein said first sequence is as set forth in SEQ ID NO: 4.

In an embodiment of the present disclosure, there is provided a recombinant host cell comprising a DNA vector as described herein, wherein said flower specific promoter is selected from the group consisting of AP3 promoter for floral expression from *Arabidopsis* (U30729), AP3 promoter for floral expression from Tomato (DQ539418.1), AP3 Promoter from *Coffea Arabica* (AHW58030.1), TA29 Promoter for Tapetum-specific expression from *Lycopersicon esculentum* (AM261325.1), and TA29 Promoter from Tobacco for Tapetum-specific expression (X52283). The developmentally regulated APETALA3 promoter from *Arabidopsis thaliana* (AP3) which is specific to petals and stamens, (Jack, T. et al. (1994) Cell 76, 703-716); AP3 was chosen as a tissue specific promoter because it is expressed very early in the development of the stamen (as well as the petal).

In an embodiment of the present disclosure, there is provided a recombinant host cell comprising a DNA vector as described herein, wherein said anther specific promoter sequence is as set forth in SEQ ID NO: 5.

In an embodiment of the present disclosure, there is provided a recombinant host cell comprising a DNA vector, said DNA vector comprising a DNA construct, said DNA construct comprising a polynucleotide fragment, said polynucleotide fragment comprising a first, and a second sequence, wherein said first sequence encodes a mitochondrial transit peptide having amino acid sequence as set forth in SEQ ID NO: 2, and said second sequence encodes a polypeptide having amino acid sequence as set forth in SEQ ID NO: 1, and said polynucleotide fragment is operably linked to a flower specific promoter having sequence as set forth in SEQ ID NO: 5.

In an embodiment of the present disclosure, there is provided a recombinant host cell comprising a DNA vector, said DNA vector comprising a DNA construct, said DNA construct comprising a polynucleotide fragment, said polynucleotide fragment comprising a first, and a second sequence, wherein said first sequence encodes a mitochondrial transit peptide encoded by a sequence as set forth in SEQ ID NO: 4, and said second sequence as set forth in SEQ ID NO: 3, and said polynucleotide fragment is operably linked to a flower specific promoter having sequence as set forth in SEQ ID NO: 5.

In an embodiment of the present disclosure, there is provided a recombinant host cell comprising a DNA vector as described herein, wherein said recombinant host cell is a fungal cell.

In an embodiment of the present disclosure, there is provided a recombinant host cell comprising a DNA vector as described herein, wherein said recombinant host cell is a bacterial cell.

In an embodiment of the present disclosure, there is provided a recombinant host cell comprising a DNA vector as described herein, wherein said recombinant host cell is *Agrobacterium*.

In an embodiment of the present disclosure, there is provided a recombinant host cell comprising a DNA vector as described herein, wherein said recombinant host cell is *Agrobacterium tumefaciens*.

In an embodiment of the present disclosure, there is provided a male sterile plant harboring in its genome a DNA construct comprising a polynucleotide fragment, said polynucleotide fragment comprising a first, and a second sequence, wherein said first sequence encodes a mitochondrial transit peptide, said second sequence encodes a polypeptide having amino acid sequence as set forth in SEQ ID NO: 1, and said polynucleotide fragment is operably linked to a flower or anther specific promoter.

In an embodiment of the present disclosure, there is provided a male sterile plant as described herein, wherein said second sequence is as set forth in SEQ ID NO: 3.

In an embodiment of the present disclosure, there is provided a male sterile plant as described herein, wherein said mitochondrial transit peptide is selected from the group consisting of mitochondrial transit peptide of the cytochrome oxidase subunit IV from yeast, and COX4 from *Saccharomyces cerevisiae* (P04037|1-25).

In an embodiment of the present disclosure, there is provided a male sterile plant as described herein, wherein said mitochondrial transit peptide amino acid sequence is as set forth in SEQ ID NO: 2, and is fused in-frame at the 5' end of said second sequence.

In an embodiment of the present disclosure, there is provided a male sterile plant as described herein, wherein said mitochondrial transit peptide amino acid sequence is as set forth in SEQ ID NO: 2, and is fused in-frame at the 5' end of SEQ ID NO: 1.

In an embodiment of the present disclosure, there is provided a male sterile plant as described herein, wherein said first sequence is as set forth in SEQ ID NO: 4.

In an embodiment of the present disclosure, there is provided a male sterile plant as described herein, wherein said flower specific promoter is selected from the group consisting of AP3 promoter for floral expression from *Arabidopsis* (U30729), AP3 promoter for floral expression from Tomato (DQ539418.1), AP3 Promoter from *Coffea Arabica* (AHW58030.1), TA29 Promoter for Tapetum-specific expression from *Lycopersicon esculentum* (AM261325.1), and TA29 Promoter from Tobacco for Tapetum-specific expression (X52283). The developmentally regulated APETALA3 promoter from *Arabidopsis thaliana* (AP3) which is specific to petals and stamens, (Jack, T. et al. (1994) Cell 76, 703-716); AP3 was chosen as a tissue specific promoter because it is expressed very early in the development of the stamen (as well as the petal).

In an embodiment of the present disclosure, there is provided a male sterile plant as described herein, wherein said flower specific promoter sequence is as set forth in SEQ ID NO: 5.

In an embodiment of the present disclosure, there is provided a male sterile plant harboring in its genome a DNA construct, said DNA construct comprising a polynucleotide fragment, said polynucleotide fragment comprising a first, and a second sequence, wherein said first sequence encodes a mitochondrial transit peptide having amino acid sequence as set forth in SEQ ID NO: 2, and said second sequence encodes a polypeptide having amino acid sequence as set forth in SEQ ID NO: 1, and said polynucleotide fragment is operably linked to an flower specific promoter having sequence as set forth in SEQ ID NO: 5.

In an embodiment of the present disclosure, there is provided a male sterile plant harboring in its genome a DNA construct, said DNA construct comprising a polynucleotide fragment, said polynucleotide fragment comprising a first, and a second sequence, wherein said first sequence encodes a mitochondrial transit peptide encoded by a sequence as set forth in SEQ ID NO: 4, and said second sequence as set forth in SEQ ID NO: 3, and said polynucleotide fragment is operably linked to an flower specific promoter having sequence as set forth in SEQ ID NO: 5.

In an embodiment of the present disclosure, there is provided a male sterile plant as described herein, wherein said plant is a monocot.

In an embodiment of the present disclosure, there is provided a male sterile plant, wherein said plant is a dicot.

In an embodiment of the present disclosure, there is provided a male sterile plant, wherein said plant is selected from the group consisting of kidney bean, lima bean, mung bean, black gram, broad bean, field bean, garden pea, chickpea, black eyed pea, pigeonpea, tobacco, rice, maize, wheat, sorghum, and lentil.

In an embodiment of the present disclosure, there is provided a male sterile plant, wherein said plant is *Arabidopsis*.

In an embodiment of the present disclosure, there is provided a male sterile plant, wherein said plant is tobacco or pigeonpea.

In an embodiment of the present disclosure, there is provided a method of obtaining a male sterile plant, said method comprising: (a) obtaining a DNA construct comprising a first, and a second sequence, wherein said first sequence encodes a mitochondrial transit peptide, said second sequence encodes a polypeptide having amino acid sequence as set forth in SEQ ID NO: 1, and said polynucleotide fragment is operably linked to an flower specific promoter; or a recombinant host cell comprising a DNA vector, said DNA vector comprising said DNA construct; (b) transforming plant cells with said DNA construct or recombinant host cell; and (c) selecting and developing a transgenic plant capable of heterologously expressing a polypeptide having amino acid sequence as set forth in SEQ ID NO: 6, wherein said plant is a male sterile plant.

In an embodiment of the present disclosure, there is provided a method of obtaining a male sterile plant as described herein, wherein said recombinant host cell is *Agrobacterium*.

In an embodiment of the present disclosure, there is provided a method of obtaining a male sterile plant as described herein, wherein transformation is carried out by a method selected from the group consisting of *Agrobacterium* mediated transformation method, particle gun bombardment method, in-planta transformation method, liposome mediated transformation method, protoplast transformation method, microinjection, and macroinjection.

In an embodiment of the present disclosure, there is provided a method of obtaining a male sterile plant as described herein, wherein transformation is carried out by *Agrobacterium* mediated transformation method.

In an embodiment of the present disclosure, there is provided a method of obtaining a male sterile plant as described herein, wherein transformation is carried out by particle gun bombardment method.

In an embodiment of the present disclosure, there is provided a method of obtaining a male sterile plant as described herein, wherein said second sequence is as set forth in SEQ ID NO: 3.

In an embodiment of the present disclosure, there is provided a method of obtaining a male sterile plant as described herein, wherein said mitochondrial transit peptide is selected from the group consisting of mitochondrial transit peptide of the cytochrome oxidase subunit IV from yeast, and COX4 from *Saccharomyces cererisiae* (P04037|1-25).

In an embodiment of the present disclosure, there is provided a method of obtaining a male sterile plant as described herein, wherein said mitochondrial transit peptide amino acid sequence is as set forth in SEQ ID NO: 2, and is fused in-frame at the 5' end of said second sequence.

In an embodiment of the present disclosure, there is provided a method of obtaining a male sterile plant as described herein, wherein said mitochondrial transit peptide amino acid sequence is as set forth in SEQ ID NO: 2, and is fused in-frame at the 5' end of SEQ ID NO: 1.

In an embodiment of the present disclosure, there is provided a method of obtaining a male sterile plant as described herein, wherein said first sequence is as set forth in SEQ ID NO: 4.

In an embodiment of the present disclosure, there is provided a method of obtaining a male sterile plant as described herein, wherein said flower specific promoter is selected from the group consisting of AP3 promoter for floral expression from *Arabidopsis* (U30729), AP3 promoter for floral expression from Tomato (DQ539418.1), AP3 Promoter from *Coffea Arabica* (AHW58030.1), TA29 Promoter for Tapetum-specific expression from *Lycopersicon esculentum* (AM261325.1), and TA29 Promoter from Tobacco for Tapetum-specific expression (X52283). The developmentally regulated APETALA3 promoter from *Arabidopsis thaliana* (AP3) which is specific to petals and stamens, (Jack, T. et al. (1994) Cell 76, 703-716); AP3 was chosen as a tissue specific promoter because it is expressed very early in the development of the stamen (as well as the petal).

In an embodiment of the present disclosure, there is provided a method of obtaining a male sterile plant as described herein, wherein said flower specific promoter sequence is as set forth in SEQ ID NO: 5.

In an embodiment of the present disclosure, there is provided a method of obtaining a male sterile *Arabidopsis* plant, said method comprising: (a) obtaining a DNA construct comprising a polynucleotide fragment, said polynucleotide fragment comprising a first, and a second sequence, wherein said first sequence encodes a mitochondrial transit peptide having amino acid sequence as set forth in SEQ ID NO: 2, and said second sequence encodes a polypeptide having amino acid sequence as set forth in SEQ ID NO: 1, and said polynucleotide fragment is operably linked to a flower specific promoter having sequence as set forth in SEQ ID NO: 5; (b) transforming *Arabidopsis* cells with said DNA construct by particle gun bombardment method; and (c) selecting and developing a transgenic *Arabidopsis* plant capable of heterologously expressing a polypeptide having amino acid sequence as set forth in SEQ ID NO: 6, wherein said *Arabidopsis* plant is a cytoplasmic male sterile *Arabidopsis* plant.

In an embodiment of the present disclosure, there is provided a method of obtaining a male sterile tobacco plant, said method comprising: (a) obtaining a DNA construct comprising a polynucleotide fragment, said polynucleotide fragment comprising a first, and a second sequence, wherein said first sequence encodes a mitochondrial transit peptide having amino acid sequence as set forth in SEQ ID NO: 2, and said second sequence encodes a polypeptide having amino acid sequence as set forth in SEQ ID NO: 1, and said polynucleotide fragment is operably linked to a flower specific promoter having sequence as set forth in SEQ ID NO: 5; (b) transforming tobacco cells with said DNA construct by particle gun bombardment method; and (c) selecting and developing a transgenic tobacco plant capable of heterologously expressing a polypeptide having amino acid sequence as set forth in SEQ ID NO: 6, wherein said tobacco plant is a male sterile tobacco plant.

In an embodiment of the present disclosure, there is provided a method of obtaining a cytoplasmic male sterile pigeonpea plant, said method comprising: (a) obtaining a DNA construct comprising a polynucleotide fragment, said polynucleotide fragment comprising a polynucleotide fragment, said polynucleotide fragment comprising a first, and a second sequence, wherein said first sequence encodes a mitochondrial transit peptide encoded by a sequence as set forth in SEQ ID NO: 4, and said second sequence as set forth in SEQ ID NO: 3, and said polynucleotide fragment is operably linked to a flower specific promoter having sequence as set forth in SEQ ID NO: 5; (b) transforming pigeonpea cells with said DNA construct by particle gun bombardment method; and (c) selecting and developing a transgenic pigeonpea plant capable of heterologously expressing a polypeptide having amino acid sequence as set forth in SEQ ID NO: 6, wherein said pigeonpea plant is a cytoplasmic male sterile pigeonpea plant.

In an embodiment of the present disclosure, there is provided a method of obtaining a male sterile tobacco plant, said method comprising: (a) obtaining a DNA construct comprising a polynucleotide fragment, said polynucleotide fragment comprising a first, and a second sequence, wherein said first sequence encodes a mitochondrial transit peptide encoded by a sequence as set forth in SEQ ID NO: 4, and said second sequence as set forth in SEQ ID NO: 3, and said polynucleotide fragment is operably linked to a flower specific promoter having sequence as set forth in SEQ ID NO: 5; (b) transforming tobacco cells with said DNA construct by particle gun bombardment method; and (c) selecting and developing a transgenic tobacco plant capable of heterologously expressing a polypeptide having amino acid sequence as set forth in SEQ ID NO: 6, wherein said tobacco plant is a male sterile tobacco plant.

In an embodiment of the present disclosure, there is provided a method of obtaining a male sterile *Arabidopsis* plant, said method comprising: (a) obtaining an *Agrobacterium* host cell comprising a DNA vector, said DNA vector comprising a DNA construct, said DNA construct comprising a polynucleotide fragment, said polynucleotide fragment comprising a first, and a second sequence, wherein said first sequence encodes a mitochondrial transit peptide having amino acid sequence as set forth in SEQ ID NO: 2, and said second sequence encodes a polypeptide having amino acid sequence as set forth in SEQ ID NO: 1, and said polynucleotide fragment is operably linked to a flower specific promoter having sequence as set forth in SEQ ID NO: 5; (b) transforming *Arabidopsis* cells with said host cell by *Agrobacterium* mediated transformation method; and (c) selecting and developing a transgenic pigeonpea plant capable of heterologously expressing a polypeptide having amino acid sequence as set forth in SEQ ID NO: 6, wherein said *Arabidopsis* plant is a cytoplasmic male sterile *Arabidopsis* plant.

In an embodiment of the present disclosure, there is provided a method of obtaining a male sterile tobacco plant, said method comprising: (a) obtaining an *Agrobacterium* host cell comprising a DNA vector, said DNA vector comprising a DNA construct, said DNA construct comprising a polynucleotide fragment, said polynucleotide fragment comprising a first, and a second sequence, wherein said first sequence encodes a mitochondrial transit peptide having amino acid sequence as set forth in SEQ ID NO: 2, and said second sequence encodes a polypeptide having amino acid sequence as set forth in SEQ ID NO: 1, and said polynucleotide fragment is operably linked to a flower specific promoter having sequence as set forth in SEQ ID NO: 5; (b) transforming tobacco cells with said host cell by *Agrobacterium* mediated transformation method; and (c) selecting and developing a transgenic tobacco plant capable of heterologously expressing a polypeptide having amino acid sequence as set forth in SEQ ID NO: 6, wherein said tobacco plant is a male sterile tobacco plant.

In an embodiment of the present disclosure, there is provided a method of obtaining a cytoplasmic male sterile *Arabidopsis* plant, said method comprising: (a) obtaining an *Agrobacterium* host cell comprising a DNA vector, said DNA vector comprising a DNA construct, said DNA construct comprising a polynucleotide fragment, said polynucleotide fragment comprising a first, and a second sequence, wherein said first sequence encodes a mitochondrial transit peptide having amino acid sequence as set forth in SEQ ID NO: 2, and said second sequence encodes a polypeptide having amino acid sequence as set forth in SEQ ID NO: 1, and said polynucleotide fragment is operably linked to a flower specific promoter having sequence as set forth in SEQ ID NO: 5; (b) transforming *Arabidopsis* cells with said host cell by *Agrobacterium* mediated transformation method; and (c) selecting and developing a transgenic *Arabidopsis* plant capable of heterologously expressing a polypeptide having amino acid sequence as set forth in SEQ ID NO: 6, wherein said pigeonpea plant is a cytoplasmic male sterile pigeonpea plant.

In an embodiment of the present disclosure, there is provided a method of obtaining a male sterile tobacco plant, said method comprising: (a) obtaining an *Agrobacterium* host cell comprising a DNA vector, said DNA vector comprising a DNA construct, said DNA construct comprising a polynucleotide fragment, said polynucleotide fragment comprising a first, and a second sequence, wherein said first sequence encodes a mitochondrial transit peptide having amino acid sequence as set forth in SEQ ID NO: 2, and said second sequence encodes a polypeptide having amino acid sequence as set forth in SEQ ID NO: 1, and said polynucleotide fragment is operably linked to an flower specific promoter having sequence as set forth in SEQ ID NO: 5; (b) transforming tobacco cells with said host cell by *Agrobacterium* mediated transformation method; and (c) selecting and developing a transgenic tobacco plant capable of heterologously expressing a polypeptide having amino acid sequence as set forth in SEQ ID NO: 6, wherein said tobacco plant is a male sterile tobacco plant.

In an embodiment of the present disclosure, there is provided a method of identification of transgenic male sterile plants, said method comprising: (a) obtaining a transgenic plant biological material comprising DNA; (b) carrying out an amplification reaction using primers which bind to a DNA sequence as set forth in SEQ ID NO: 7 to generate amplicons; (c) detecting the presence of said amplicons, wherein presence of said amplicons is indicative of the transgenic plant being cytoplasmic male sterile.

In an embodiment of the present disclosure, there is provided a method of identification of transgenic male sterile plants as described herein, wherein said primers comprise at least one primer pair comprising a forward, and a reverse primer, wherein both forward primer and reverse primer do not substantially bind to a region as set forth in SEQ ID NO: 3.

In an embodiment of the present disclosure, there is provided a method of identification of transgenic male sterile plants as described herein, wherein said primers comprise at least one primer pair comprising a forward, and a reverse primer, wherein both forward primer and reverse primer do not substantially bind to a region as set forth in SEQ ID NO: 4.

In an embodiment of the present disclosure, there is provided a method of identification of transgenic male sterile plants as described herein, wherein said primers comprise at least one primer pair comprising a forward, and a reverse primer, wherein both forward primer and reverse primer do not substantially bind to a region as set forth in SEQ ID NO: 3 or SEQ ID NO: 4.

In an embodiment of the present disclosure, there is provided a method of identification of transgenic male sterile plants as described herein, wherein said primers comprise at least one primer pair comprising a forward, and a reverse primer, wherein said forward primer substantially binds to a region as set forth in SEQ ID NO: 3, and said reverse primer substantially binds to a region as set forth in SEQ ID NO: 4.

In an embodiment of the present disclosure, there is provided a method of identification of transgenic male sterile plants as described herein, wherein said primers comprise at least one primer pair comprising a forward, and a reverse primer, wherein said forward primer substantially binds to a region as set forth in SEQ ID NO: 4, and said reverse primer substantially binds to a region as set forth in SEQ ID NO: 3.

In an embodiment of the present disclosure, there is provided a method of identification of transgenic male sterile plants as described herein, wherein said transgenic plant is a monocot.

In an embodiment of the present disclosure, there is provided a method of identification of transgenic male sterile plants as described herein, wherein said transgenic plant is a dicot.

In an embodiment of the present disclosure, there is provided a method of identification of transgenic male sterile plants as described herein, wherein said transgenic plant is selected from the group consisting of kidney bean, lima bean, mung bean, black gram, broad bean, field bean, garden pea, chick pea, black eyed pea, pigeonpea, tobacco, rice, maize, wheat, sorghum, and lentil.

In an embodiment of the present disclosure, there is provided a method of identification of transgenic cytoplasmic male sterile plants as described herein, wherein said transgenic plant is pigeonpea or lentil.

In an embodiment of the present disclosure, there is provided a method of identification of transgenic cytoplasmic male sterile plants as described herein, wherein said transgenic plant is tobacco.

In an embodiment of the present disclosure, there is provided an isolated polynucleotide fragment comprising a first, and a second sequence, wherein the first sequence encodes a mitochondrial transit peptide, and said second sequence encodes a polypeptide having amino acid sequence as set forth in SEQ ID NO: 1.

In an embodiment of the present disclosure, there is provided an isolated polynucleotide fragment as describe herein, wherein said second sequence is as set forth in SEQ ID NO: 3.

In an embodiment of the present disclosure, there is provided an isolated polynucleotide fragment as describe herein, wherein said mitochondrial transit peptide is selected from the group consisting of mitochondrial transit peptide of the cytochrome oxidase subunit IV from yeast, and COX4 from *Saccharomyces cerevisiae* (P04037|1-25).

In an embodiment of the present disclosure, there is provided an isolated polynucleotide fragment as describe herein, wherein said mitochondrial transit peptide amino acid sequence is as set forth in SEQ ID NO: 2.

In an embodiment of the present disclosure, there is provided an isolated polynucleotide fragment as describe herein, wherein said mitochondrial transit peptide is encoded by SEQ ID NO: 4.

In an embodiment of the present disclosure, there is provided an isolated polynucleotide fragment as describe herein, wherein said polynucleotide fragment sequence is as set forth in SEQ ID NO: 7.

In an embodiment of the present disclosure, there is provided an isolated polynucleotide fragment as describe herein, wherein said polynucleotide fragment encodes a polypeptide having amino acid sequence as set forth in SEQ ID NO: 6.

In an embodiment of the present disclosure, there is provided an isolated polynucleotide fragment as described here in, for use in generating male sterile plants.

In an embodiment of the present disclosure, there is provided an isolated polynucleotide fragment as described here in, for use in detection of male sterile plants comprising a polynucleotide fragment, said polynucleotide fragment comprising a first, and a second sequence, wherein said first sequence encodes a mitochondrial transit peptide, said second sequence encodes a polypeptide having amino acid sequence as set forth in SEQ ID NO: 1.

In an embodiment of the present disclosure, there is provided an isolated polynucleotide fragment as described herein, wherein said second sequence is at least 80% similar to SEQ ID NO: 3.

In an embodiment of the present disclosure, there is provided an isolated polynucleotide fragment as described herein, wherein said second sequence is at least 80%, 81%, 82%, 83%, 84%, 85%, 86%, 87%, 88%, 89%, 90%, 91%, 92%, 93%, 94%, 95%, 96%, 97%, 98%, or 99% similar to SEQ ID NO: 3.

In an embodiment of the present disclosure, there is provided an isolated polynucleotide fragment as described herein, wherein said fragment is derived from *Cajanus cajan* (L.) Millsp. (Pigeonpea).

In an embodiment of the present disclosure, there is provided a method of inhibiting pollen production in plants, said method comprising transforming plant cells with a DNA construct or a recombinant host cell, said DNA construct or host cell as described herein.

In an embodiment of the present disclosure, there is provided an isolated polynucleotide fragment encoding a protein involved in restoration of cytoplasmic male sterility in pigeonpea.

In an embodiment of the present disclosure, there is provided a method of producing synthetic restorers by genetic transformation, said method comprising: (a) isolating DNA fragment having at least 90% homology to a DNA fragment encoding a polypeptide having a signal peptide sequence for translocation of said polypeptide to mitochondria, wherein said polypeptide is involved in restoration of fertility of a male sterile plant, selected from the group consisting of 14 or more pentatricopeptide repeats; and (b) transforming a monocot or dicot plant cell(s) with a DNA construct comprising said DNA fragment from step (a) or recombinant host cell comprising said DNA construct.

In an embodiment of the present disclosure, there is provided a method of developing hybrid plant in a monocot or dicot plant species by crossing the transgenic male sterile plant with a plant in which the fertility restoring gene is capable of restoring male sterility, wherein said male sterile plant is as described herein.

In an embodiment of the present disclosure, there is provided a method to modify pollen production of sterile lines which can be used in monocot or dicot plant species.

In an embodiment of the present disclosure, there is provided a gene specific marker to trace and detect impurity in hybrid seeds of pigeonpea.

In an embodiment of the present disclosure, there is provided a gene specific marker to detect seed purity of parental lines of pigeonpea.

In an embodiment of the present disclosure there is provided a gene specific marker as described herein, wherein the gene specific marker having sequence is as set forth in SEQ ID NO. 7. In another embodiment, the SEQ ID NO. 7 comprises SEQ ID NO: 3. In yet another embodiment, the SEQ ID NO. 7 comprises SEQ ID NO: 4. In further embodiment, the SEQ ID NO. 7 comprises SEQ ID NO: 3 and SEQ ID NO: 4.

In an embodiment of the present disclosure there is provided a gene specific marker as described herein, wherein the gene specific marker encodes for a polypeptide having sequence as set forth in SEQ ID NO: 6.

In an embodiment of the present disclosure, there is provided a method for screening a population of plant with a gene specific marker having sequence as set forth in SEQ ID NO: 7, wherein said gene specific marker is linked to a cytoplasmic male sterility gene in plants. In another embodiment, the plant is pigeonpea In an embodiment of the present disclosure there is provided an isolated polynucleotide fragment encoding a protein involved in restoration of cytoplasmic male sterility in pigeonpea.

In an embodiment of the present disclosure, there is provided a method of producing synthetic restorers by genetic transformation, said method comprising: (a) isolating DNA fragment having at least 90% homology to a DNA fragment encoding a polypeptide having a signal peptide sequence for translocation of said polypeptide to mitochondria, wherein said polypeptide is involved in restoration of fertility of a male sterile plant, selected from the group consisting of 14 or more pentatricopeptide repeats; and (b) transforming a monocot or dicot plant cell(s) with a DNA construct comprising said DNA fragment from step (a) or recombinant host cell comprising said DNA construct.

In an embodiment of the present disclosure, there is provided a method of developing hybrid plant in a monocot or dicot plant species by crossing the transgenic male sterile as described herein, with a plant in which the fertility restoring gene is capable of restoring male sterility.

In an embodiment of the present disclosure, there is provided an isolated DNA encoding a protein involved in restoration of cytoplasmic male sterility to fertility in plants. In another embodiment, the plant is pigeonpea.

Although the subject matter has been described in considerable detail with reference to certain preferred embodiments thereof, other embodiments are possible.

EXAMPLES

The disclosure will now be illustrated with working examples, which is intended to illustrate the working of disclosure and not intended to take restrictively to imply any limitations on the scope of the present disclosure. Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein. It is to be understood that this disclosure is not limited to particular methods, and experimental conditions described, as such methods and conditions may vary.

Materials and Methods

Plant material: Seeds of an $A_4$ cytoplasm (*Cajanus cajanifolius*) containing CMS line, designated ICPA 2039 was procured from the Pigeonpea Breeding Unit of the International Crops Research Institute for Semi-Arid Tropics (ICRISAT) in Hyderabad, India. The plants were grown in pots containing autoclaved sand and soil (1:1) mixture, and maintained in a greenhouse under a 16/8 h light/dark cycle at 25/23° C. with 70-80% relative humidity.

Strains and plasmids: *Escherichia coli* strains were grown in Luria-Bertani (LB) medium, supplemented with kanamycin (50 μg ml$^{-1}$) or carbenicillin (100 μg ml$^{-1}$) when appropriate. The pET-19b (+) expression vector and the *E. coli* strain BL21 (DE3) pLysS (Novagen) were used for prokaryotic expression studies.

Examples

Genomic DNA extraction and genome walking: Total genomic DNA samples were prepared from the fresh leaves of one to two week-old seedlings using the NucleoSpin Plant II DNA isolation kit (Macherey-Nagel, Germany). Approximately, 500 ng of the genomic DNA was used for genome walking according to Reddy et al. (Anal. Biochem., 2008, 381, 248-253) to identify the flanking sequences. Contigs from the published pigeonpea mitochondrial genomes (Tuteja et al. DNA Res., 2013, 20, 485-495) of ICPA 2019 (male sterile) and ICPB 2039 (maintainer) were compared in silico. Based on unique rearrangement sites, a 1.291 kb region of genomic DNA upstream of the nad7 gene in both sterile and fertile lines was amplified and cloned using PCR-based directional genome walking with a cDNA sequence specific antisense primer (SEQ ID NO: 8).

RNA isolation: Total RNA was isolated from unopened flower buds and leaves from three-week old plants using Trizol (Invitrogen) and the RNeasy Plant Mini Kit (Qiagen) following the manufacturer's protocol. Total RNA was used for cDNA synthesis using the First-Strand cDNA Synthesis Kit (Invitrogen) according to the manufacturer's instructions. The concentration and purity of all RNA samples was tested using a NanoVue plus spectrophotometer (GE health care, USA) at 260/280 nm absorbance. Only samples whose absorbance ranged from 1.8 to 2.0 were selected. The integrity of the RNA was confirmed by electrophoresis on 1.4% agarose gels.

The cDNAs from ICPA 2039 (both sterile line, and fertile line) and ICPB 2039 (male sterile line) were used for the amplification of orf 133 (402 bp, SEQ ID NO:46) (using primers having sequence of SEQ ID NO: 9, and SEQ ID NO: 10), and orf 147 (444 bp, SEQ ID NO: 3) (using primers having sequence of SEQ ID NO: 11, and SEQ ID NO: 12). PCR fragments were used as templates for Re-PCR with primers (SEQ ID NO: 13, and 14 correspond to forward and reverse primers respectively for amplifying orf133; SEQ ID NO: 15, and 16 correspond to forward and reverse primers respectively for amplifying orf147) containing restriction sites at the 5' ends for cloning into a bacterial expression plasmid. The PCR fragments were cloned into the "pJET 2.1 Blunt" plasmid (Thermo) which was confirmed by sequencing. Mini-preparations were used to isolate the recombinant plasmid and the correct orientation of the insert was ascertained by restriction analysis.

Monitoring *E. coli* growth rate: Overnight-grown cultures of BL21 (DE3) pLysS (Novagen) harboring pET147, pET (133) or pET32a control plasmids were obtained by using a single colony to inoculate 1.5 ml of LB medium supplemented with carbenicillin and incubated overnight at 37° C. A flask containing 200 ml of LB medium supplemented with the same antibiotic was inoculated with 200 µl of the pre-culture and incubated at 37° C. with shaking. At an $OD_{600}$ of 0.3, the culture was separated into two equal subcultures which were induced with 0.5 mM IPTG. The growth of the cultures was monitored on an hourly basis at 600 nm using a spectrophotometer (Eppendorf Bio Photometer plus).

Vector construction: The 886 bp fragment of the *A. thaliana* flower-specific AP3 promoter (SEQ ID NO: 5) was amplified using primers AtAP3_Pro_KpnIF (SEQ ID NO: 17) and AtAP3_Pro_NdeIR (SEQ ID NO: 18) followed by cloning in pJET blunt 2.1 plasmid CoxIV (mitochondrial transit peptide of the cytochrome oxidase subunit IV from yeast) (SEQ ID NO: 4) (Köhler et al., Mol. Gen. Genet., 1997, 227, 369-376). The pre-sequence was amplified using the TSPF and TSPR primers (SEQ ID NO: 19, and 20 respectively) from *Saccharomyces cerevisiae* cDNA. The Orf147 fragment was amplified using primers Orf 147F and Orf 147 Not1R, and subsequently fused to CoxIV by overlap extension PCR using the primers OE 147F and OE 147R (SEQ ID NO: 21 (forward) and SEQ ID NO: 22 (reverse); SEQ ID NO: 23 (forward with restriction site), and SEQ ID NO: 24 (reverse with restriction site)). The PCR amplified AP3 promoter fragment (KpnI, NdeI) and Cox-orf147 fusion fragment (NdeI, NotI) were together sub-cloned into a modified pL12R34H plasmid at the KpnI, NotI site, then into pMDC100 followed by mobilization into *Agrobacterium tumefaciens* strain C58 for plant transformation studies in *Arabidopsis* and tobacco.

Plant transformation: *Arabidopsis thaliana* seeds (Col-1) were germinated in 4-cm pots and maintained in culture room conditions until the four-leaf stage. This was followed by transfer to a glasshouse where they were irrigated every four days until appearance of the inflorescences. Once the inflorescences reached about five cm, plants were transformed with *A. tumefaciens* suspension harboring the genes of interest using the floral dip protocol (Clough et al., Plant J., 1998, 16, 735-743), with inoculations repeated twice at three-day intervals. The seeds were collected at maturity. Tobacco (*Nicotiana tabacum* L., var. Xanthi) seedlings were grown under controlled sterile-environment conditions for two weeks followed by *Agrobacterium*-mediated transformation using the standard leaf disc method (Sunkara et al., Appl. Biochem. Biotechnol., 2013, 172, 325-339. DOI: 10.1007/s12010-013-0482-x). Transgenic plants were grown in pots containing autoclaved sand and soil (1:1) in a containment greenhouse until flowering and seed formation set in. A 16/8 h light/dark cycle at 23/20° C. with 65-70% relative humidity was used for *Arabidopsis* and 25/23° C. with 70-80% relative humidity for tobacco.

Molecular characterization of transgenic plants: Genomic DNA from kanamycin resistant *N. tabacum* and *A. thaliana* plants was isolated using the NucleoSpin Plant II DNA isolation kit and subjected to PCR using orf147 specific primers. PCR conditions included an initial denaturation cycle of 5 min at 94° C., followed by 35 cycles of denaturation for 30 s at 94° C., annealing for 1 min at 58° C. with an extension for 1 min at 72° C. and a final extension for 10 min at 72° C.

Candidate gene selection and primer design: Genome walking in male sterile and fertile lines as well as cDNA amplification was carried out using specific primers. Seven candidate genes were selected for qRT-PCR analysis, which included genes associated with anther biogenesis, which have key roles in normal tapetal function and viable pollen production. These were Defective in tapetal development and function (TDF1/MYB35); Aborted Microspore (AMS) (forward primer SEQ ID NO: 27; reverse primer SEQ ID NO: 28); Dysfunctional Tapetum1 (DYT1) (forward primer SEQ ID NO: 25; reverse primer SEQ ID NO: 26), and Male Sterility 1 (MS1). The other three genes which were from the lignin biosynthetic pathway viz., 4CL (4 Coumarate:CoAligase)(forward primer SEQ ID NO: 39; reverse primer SEQ ID NO: 40), CCoAOMT (Caffeoyl CoA O-Methylransferase) (SEQ ID NO: 37, and SEQ ID NO: 38), and C3H (Cinnamic acid 3-hydroxylase) (SEQ ID NO: 35, and SEQ ID NO: 36) were selected from the *Arabidopsis* database (TIAR) and used for qRT-PCR analysis. Three reference genes SAND (SEQ ID NO: 29, and SEQ ID NO: 30), TIP41 (SEQ ID NO: 31, and SEQ ID NO: 32) and UNK (SEQ ID NO: 33, and SEQ ID NO: 34), showing highly stable expression (Czechowski et al., Plant Physiol., 2005, 139, 5-17. doi:10.1104/pp. 105.063743) were selected as reference genes for this study. The retrieved *A. thaliana* sequences were used to design PCR primers using Primer 3 Plus software. The primers had a GC content of 50%, a length of 22 nucleotides and an expected product size of 80-150 base pairs.

Quantitative real time PCR analysis: All qRT-PCR reactions were carried out in a Realplex Real-Time PCR system (Eppendorf, Germany) using SYBR Green in 96 well optical reaction plates (Axygen, Union City, Calif., USA) sealed with ultra-clear sealing film (Platemax). The PCR reaction was performed in a total volume of 10 µl containing 1 µl of RNA (100 ng), 400 nM of each primer, 5 µl of 2× one step SYBR RT-PCR buffer 4 (Takara, Japan) and 0.4 µl of prime script one step Enzyme Mix 2 (Takara, Japan) made up to 10 µl with RNase-free H$_2$O. The qRT-PCR cycling conditions were as follows: 42° C. for 5 min and 95° C. for 10 s (reverse transcription) followed by 40 cycles of 15 s at 95° C., 15 s at 62° C. with fluorescent signal recording and 15 s at 72° C. The melting curve analysis was included after 40 cycles to verify the primer specificity by heating from 58° C. to 95° C. with fluorescence measured within 20 min. No-template controls were included for each of the primer combinations. All the samples were collected from the three independent plants and each sample was tested in three technical replicates. The raw quantification cycle (Cq) values of each gene were taken as the input data to estimate relative and average expression of the candidate gene using qBase plus software (ver: 2.4; Biogazelle, Belgium) (Hellemans et al., genome Biol., 2007, 8: R19. doi: 10.1186/gb-2007-8-2-r19).

Histochemical studies: The lignin content in the *A. thaliana* and *N. tabacum* flower buds was histochemically analyzed using phloroglucinol-HCl staining. The flowers were fixed in FAA solution overnight and decolorized by using ethanol 25-85% series. These were subsequently stained with 2% (w/v) phloroglucinol in 92.5% ethanol for 1 h at room temperature, following which the tissues were mounted with 18.5% (v/v) HCl. The red coloration was monitored immediately using a Leica M125 microscope (Leica Microsystems; Bannockburn; IL, USA).

Results

Figure 1:
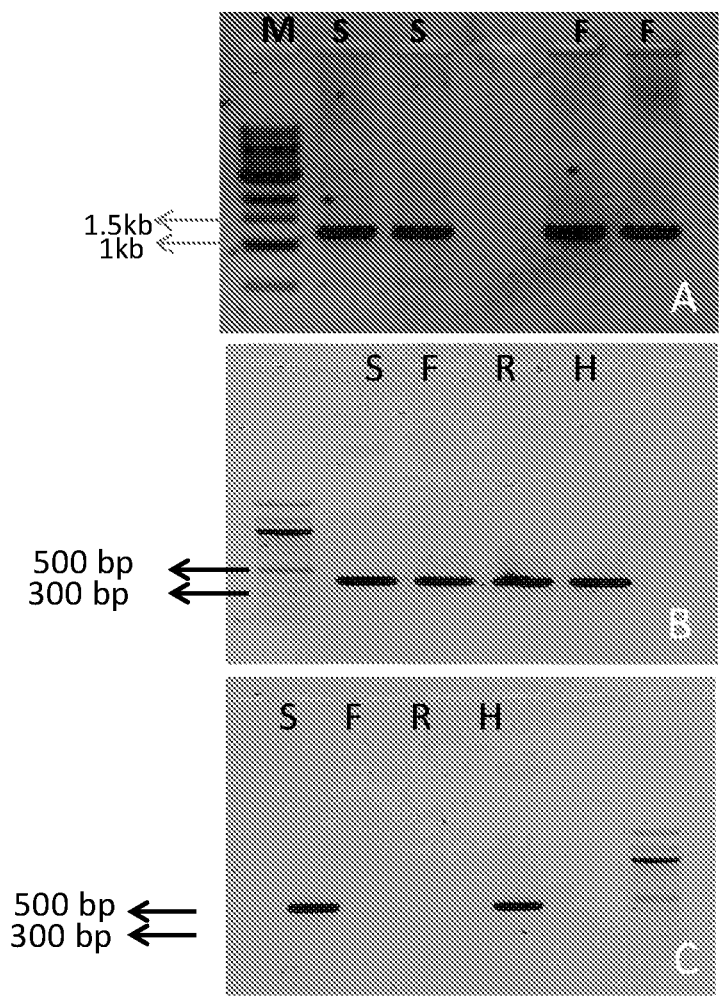
FIG. 1A depicts the RT-PCR analysis of nad7 in both male fertile, and sterile plants, in accordance with an embodiment of the present disclosure.
FIG. 1B depicts the amplification product of orf133 in parental lines and hybrid, in accordance with an embodiment of the present disclosure.
FIG. 1C depicts the amplification product of orf147 in CMS line and F1 hybrid, in accordance with an embodiment of the present disclosure.

CMS (Cytoplasmic male sterility) specific sequence in male sterile cytoplasm: To explore the CMS causing genes, previously reported rearrangement sites unique to ICPA 2039 (Tuteja et al., DNA Res., 2013, 20, 485-495), were initially compared in pigeonpea mitotypes. Interestingly, upon comparing the flanking sequences of the nad7 gene in the male sterile line with those in the maintainer line, a variable fragment was found to be located 5' to the nad7 subunit of complex I (the main dehydrogenase of the mitochondrial respiratory chain) in the male sterile line of pigeonpea. While genome walking revealed sequence variations in the 5' upstream region of nad7 of male fertile and sterile lines, the coding as well as the 3' regions were observed to be identical (FIG. 1A). Sequence divergence was observed in the upstream region starting from −259 bp of the nad7 initiation site. In FIG. 1A, M refers to protein marker ladder; S refers to male sterile line, while F refers to fertile line.

ORF prediction and expression validation by RT-PCR: Predictive analyses of nucleotide sequences of the nad7 region in the fertile parent, ICPB 2039, and in the ICPA 2039-CMS line revealed two ORFs based on a threshold of 85 amino acids, with a reasonably high level of variability. Reverse transcription-PCR (RT-PCR) analysis using different sets of primers resulted in amplification of various regions including ORF sequences upstream of the nad7 gene. cDNAs of both fertile and sterile pigeonpea lines amplified a 402 bp fragment referred to as orf133 (FIG. 1B), revealing three amino acid differences between the fertile and sterile lines (data not shown). In FIGS. 1B, and 1C, S refers to male sterile plant, F refers to fertile plant, R refers to restorer plant, while H refers to hybrid plant. However, primer set (SEQ ID NO: 11, and 12) resulted in the amplification of 444 bp fragment specific only to the male sterile line (ICPA 2039), hereby called as orf147 (SEQ ID NO: 3) (FIG. 1C). A database search for the similarity of the orf147 gene fragment from the sterile line to known ORFs in the database using BLASTX (www.ncbi.nlm.nih.gov/BLAST) detected no significant sequence homology.

Figure 2A:
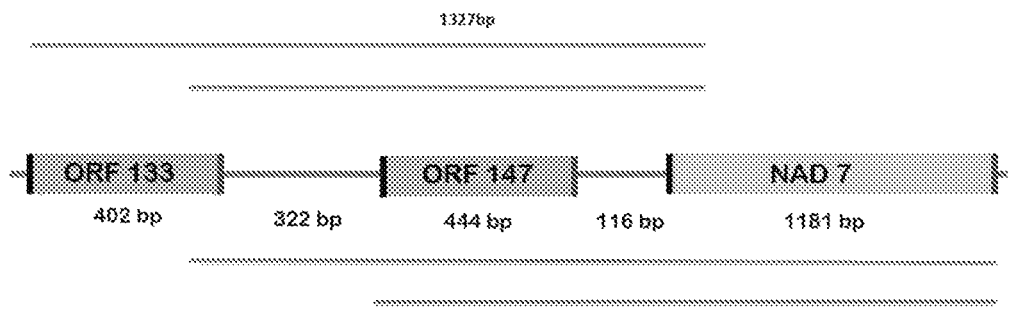
FIG. 2A depicts the organization of mitochondrial genomic regions associated with the orf147 gene in the male sterile pigeonpea line (ICPA 2039), in accordance with an embodiment of the present disclosure.
Figure 2B:
FIG. 2B depicts the amplification of 1,327 bp (left) and 1,005 bp (right) regions spanning orf133, orf147 and part of the nad7 cds (coding DNA sequence) in male sterile line and hybrid, in accordance with an embodiment of the present disclosure.
Figure 2C:
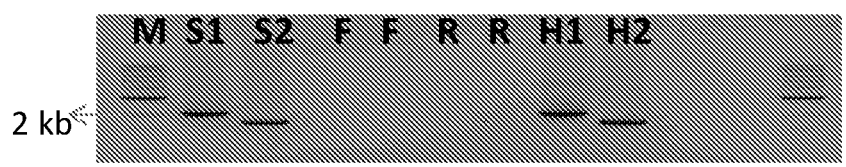
FIG. 2C depicts the amplification of 2,143 bp (S1 & H1) and 1,741 bp (S2 & H2) regions spanning the orf133, orf147 and nad7 cds in the male sterile line and hybrid, in accordance with an embodiment of the present disclosure.

However, its deduced amino acid sequence showed partial homology to "orf124" of *Beta vulgaris* subsp. maritime genotype male-sterile E mitochondrion (accession #FQ014226.1).

orf147 transcription is polycistronic: RT-PCR carried out using primer combinations specific to different internal regions viz. orf147F (SEQID NO:11)/nad7PGER (SEQID NO: 41), orf133F (SEQ ID NO: 9)/nad7P1R (SEQID NO:42), and orf133F (SEQID NO: 9)/nad7PGER (SEQID NO: 41) resulted in amplification of 1,741 bp, 1,327 bp, and 2,143 bp, respectively. These overlapping amplicons indicated the presence of a single 2,455 bp polycistronic transcript in the mitochondria from the sterile cytoplasm encompassing orf133, orf147 and nad7 and spacer sequences (FIG. 2A) In contrast, the fertile maintainer line did not show any amplification with any of these primer sets, indicating the monocistronic nature of the nad7 transcript (FIG. 2 B-C). (in FIGS. 2B & C, S refers to sterile plant, F refers to fertile plant, R refers to restorer plant, while H refers to hybrid plant). Nevertheless, orf133 amplification with gene-specific primers (orf133-F/orf133-R) in the maintainer line indicated its existence as a separate transcript (FIG. 1B).

These results were further confirmed by transcription start site (TSS) identification in the male sterile and fertile pigeonpea lines carried out using two different sets of RACE Primers. While PCR with primers RACE F1 (SEQID NO:43) and RACE R1 (SEQID NO:44) following cDNA circularization, resulted in amplification in both male sterile (ICPA2039) and maintainer (ICPB2039) lines, the primers RACE F1 and RACE R2 (SEQID NO:45) showed amplification with the male sterile line (ICPA 2039) only, thereby indicating absence of this region in the cDNA transcript (FIG. 3A). For the male sterile line (ICPA 2039), the sequence results using RACE F1 and RACE R2 (referred to as ICPA "transcript 1") identified a T residue located 1,681 bp upstream to the Nad7 start codon as the TSS (FIG. 3A), while the product of RACE F1 and RACE R1 (referred to as "transcript 2") showed a G at 656 bp upstream of the nad7A start codon as the other functional TSS (FIG. 3B), with "orf147" in common. For the male fertile maintainer line (ICPB 2039), the sequence analysis revealed the TSS at T (−556) with primers RACE F1 and RACE R1 (FIG. 3C). These results confirmed that the orf147 transcripts in the male sterile line existed with more than one cistron, while the male fertile line had a monocistronic transcript (FIG. 3D).

RNA editing and secondary structure of orf147: The cDNA sequence of the 5' upstream region of the nad7 gene in both male sterile and fertile lines were compared with their respective mitochondrial genome sequences and the genome-walked PCR products. This identified a differential RNA editing pattern in the sequenced clones for each line. Several consistent edited sites among independent clones were detected for each line. The male sterile line (ICPA 2039) exhibited 10 edited changes in this region, in contrast to 22 observed in the maintainer line. There were four edited events in the CMS line in orf133: a glycine residue at the 59 aa residue position was edited to serine; glutamine at 119 was edited to leucine; serine at 124 was changed to arginine and isoleucine at position 125 was edited to lysine. However, there was no edited event observed in orf147.

The secondary structure of the orf147 transcripts of the CMS line revealed a perfect hairpin loop structure at the 5 end (FIG. 4A). In silico analysis using a homology-based modeling program (www.expasy.org) suggested that the product of orf147 does not contain any trans-membrane domain and might be a soluble protein (FIG. 4B).

orf147 encodes a cytotoxic peptide: To examine the function of the orf147 and orf133 transcripts, their coding sequences were cloned into the expression region of the PET32a vector, followed by IPTG-induced expression in *E. coli*. While the growth curve analysis of orf133 expressing cells showed no apparent effect on growth upon IPTG induction, induction of orf147 expressing cells resulted in cytotoxicity to the *E. coli* cells (FIG. 5A, B) (in FIG. 5A, pET32a UI refers to uninduced control vector, pER32a I refers to induced control vector, Orf147 pET32a UI refers to uninduced vector comprising orf147, and Orf147A pER32a I refers to induced vector comprising orf147) (in FIG. 5B, pET32a UI refers to uninduced control vector, pER32a I refers to induced control vector, pER32a ORF133UI refers to uninduced vector comprising orf133, and pET32a ORF133 I refers to induced vector comprising orf133). The induction levels of orf147 (with His tag), and orf133 (with His tag) were also visualized by resolving the fusion proteins on 12% SDS-PAGE gel. As seen in FIG. 5A, lane 1 depicts pET 32a uninduced; lane 2 depicts pET 32a induced; lane 3 depicts orf147 pET 32a uninduced; and lane 4 depicts ORF147 pET 32a induced. In FIG. 5B, lane 1 depicts pET 32a uninduced; lane 2 depicts pET 32a induced; lane 3 depicts ORF133 pET 32a uninduced; and lane 4 depicts orf133 pET 32a induced.

Bacterial cell growth was also ascertained by evaluating colony growth of transformed bacteria in agar plates upon 0.5 mM IPTG induction and growth monitored on an hourly basis at 600 nm using a spectrophotometer. As seen in FIG. 5C, pET32a control without induction (vector alone), and pET32a Orf133 without induction show no decrease in cell density/growth. Similarly, pET32a Orf147 without induction also does not show any cell density/growth defect compared to control. pET32a Orf133 when induced, did not show any growth defect when compared to induced control pET32a (vector alone). However, pET32a Orf147 upon induction showed a severe growth defect compared to induced control pET32a (vector alone), further supporting the conclusion that expression of Orf147 is toxic to transformed *E. coli* cells.

Expression of orf147 in *Arabidopsis* and tobacco results in male sterility: Transformation with the AP3::CoxIV-Orf147 gene cassette (FIG. 6A) carrying the cox/V-orf147 gene fusion driven by the AtAP3 promoter, resulted in 24 primary transgenic events in *Arabidopsis*, and over 20 in tobacco. These were grown to maturity and T1 seeds collected. Vegetative growth of the transgenic plants (ie, growth rate and plant morphology) was uniform and similar to that of the untransformed counterparts in both species.

About 80% of the T1 progeny from the selected 12 independent *Arabidopsis* events at flowering, exhibited the semi-sterile or sterile phenotype, resulting in poor seed setting when compared to the wild type (WT) (FIG. 6 B-C) (FIG. 6B depicts male sterile transgenic *Arabidopsis* plant showing normal growth and development; FIG. 6C depicts wild type plant with primary branches showing normal siliques). At the dehiscent stage, the sterile transgenic events did not produce any pollen grains and normal siliques. The sterile plants had flowers with smaller sepals and petals than their WT counterparts, with a protruding pistil and shortened stamen filaments with impaired anther dehiscence. The semi-sterile plants bore two kinds of siliques, one shorter and with no or fewer seeds than the WT and the other normal siliques like the WT. The male sterile plants had very short siliques with no seeds (FIG. 6 D-F) (FIG. 6D depicts male sterile transgenic plant with short siliques indicating no developing seeds (top); FIG. 6E depicts front view of normal mature flowers of WT (inset shows normal anther dehiscence); and FIG. 6F depicts flowers of male sterile line revealed fused carpels, protruding pistil and short filaments (inset non-dehiscent anther in the transgenic flower)).

Similarly, out of 20 primary transgenic events of tobacco, four confirmed positive events showed complete male sterility. The flowers of male sterile transgenic tobacco plants expressing orf147 were again relatively smaller with shortened filaments and either produced very small fruits exhibiting partial sterility or had detached collapsed capsules in the completely sterile plants (FIG. 6 G-J) (FIG. 6G depicts flower size, color and structure in the WT tobacco plant; FIG. 6H depicts flowers of male sterile tobacco plants having anthers below the stigma; FIG. 6I depicts Top: Seed capsules from *N. tabacum* (WT); Bottom: Sterile progeny; and FIG. 6J depicts Seed capsules of WT plants (Left), collapsed and detached seed capsules in partially sterile transgenic phenotypes (Inset) Floral branches from wild type (WT)).

The qRT-PCR analysis of several selected transgenic *Arabidopsis* and tobacco plants revealed variation in the orf147 transcript levels, with male sterile phenotypes showing strong orf147 expression (FIG. 7 A, B). In FIG. 7A, ICPA2039 refers to a male sterile pigeonpea plant showing high relative expression of orf147, while ICPB 2039 is a fertile pigeonpea plant showing negligible orf147 expression. These data show that orf147 gene expression is associated and limited to male sterile plants only in pigeonpea. In FIG. 7B, the left column depicts orf147 expression in transgenic *Arabidopsis* which are fully male sterile, while the right column depicts orgf147 expression in transgenic tobacco, which are partially male sterile, showing that heterologous expression of orf147 in mitochondria of transgenic *Arabidopsis* or tobacco results in male sterility.

Expression of anther development related-genes: To detect the expression of anther development-related genes that act after tapetal specification, quantitative RT-PCR analysis for key genes involved in another development was carried out in male sterile and fertile pigeonpea lines (ICPA 2039 and ICPB 2039 respectively) and in transgenic *Arabidopsis* plants along with their WT. Interestingly, in the CMS pigeonpea line, while the transcripts of Defective in tapetal development and function (TDF1/MYB35), Dysfunctional tapetum1 (DYT1), and Male sterility1 (MS1) were significantly down-regulated compared with those in the fertile maintainer line, an increased accumulation of transcripts of the Aborted microspore (AMS) gene was observed (FIG. 8A).

Similarly, the ectopic expression of orf147 in *Arabidopsis* transgenic plants resulted in significant down-regulation of the transcripts of AMS and MS1 that are required for normal tapetal function and pollen wall development (FIG. 8B). This data suggested that mitochondrial expression of orf147 from the pigeonpea male sterile line induces male sterility in transgenic *Arabidopsis* plants, possibly by regulating the transcriptional expression of key genes specific to another development.

Male sterile anthers have reduced endothecium secondary wall liginifcation: Investigation of lignification patterns using phloroglucinol staining of anthers of both wild-type and transgenic male sterile flowers of *Arabidopsis* and tobacco revealed a high degree of phloroglucinol stain accumulation in the WT anthers at all stages of development, when compared to the anthers of the male sterile transgenic line (FIG. 9A-F).

Further, these observations correlated well with the gene expression profiles of key genes that are involved in lignin biosynthesis like 4CL(4 coumarate:CoAligase), CCoAOMT (caffeoyl CoA O-methyltransferase), and C3H (cinnamic acid 3-hydroxylase). Clearly, these genes were expressed at significantly lower levels in the flowers of the male sterile line when compared to the WT. The relative expression of 4CL, C3H, CCoAOMT were 0.85, 0.55 and 0.8 in male sterile plants, as compared to 1.18, 1.7 and 1.25 in the WT plants (FIG. 9G).

CONCLUSIONS

The transcription and translation patterns of the predicted ORFs in the contigs spanning a 10 kb region situated upstream and downstream of the known nad7 gene were comprehensively evaluated in the mitochondrial genomes of pigeonpea genotypes ICPA 2039 and ICPB 2039. In the present disclosure, there is disclosed a 444 bp long unique CMS-associated novel orf147 (SEQ ID NO: 3) detected upstream of and co-transcribing with the known nad7 gene in the mitochondrial genome of pigeonpea male sterile ICPA 2039 cytoplasm is very likely to be responsible for mitochondrial dysfunction. There is no indication of the novel transcript resulting in a reduced/loss or gain of function change in the nad7 gene per se indicating no apparent bearing on the oxidative phosphorylation.

The results of the present disclosure contradict and diverge from a recent report (Sinha et al., Plant Genome, 2015, Genome 8: 1-12. doi: 10.3835/plantgenome2014.11.0084), where a frame-shift mutation in the nad7 gene and the resulting disordered predicted protein structure was reported to be the cause of CMS in pigeonpea. However, these claims on the aberration in the nad7 gene, prediction of a chimeric ORF as the sterility factor causing conformational changes in the secondary and tertiary nad7 protein structure lacked experimental evidences. Besides, the cDNA clones of nad7 from CMS and fertile pigeonpea lines did not reveal any differences in the sequence and expression of nad7 and/or deduced protein structures in our study. The present data on the structural and functional variations in the male sterile and fertile lines, comprehensive characterization of the causal ORF, and its functional validation in both prokaryotic and eukaryotic biological systems clearly disagree with the conformational differences and interpretations drawn by Sinha et al., 2015 and calls for a thorough methodological review of the ORF and protein prediction analyses in Sinha et al., 2015.

The secondary structure of orf147 transcripts of the male sterile pigeonpea line reveal a perfect hairpin loop structure at the 5 end that was previously suggested to provide stability to the male sterility-associated transcripts in CMS.

Orf147 is a soluble protein cytotoxic to $E.$ $coli$ and its recombinant transgene leads to male sterility in two tested model plant species. To eliminate the possibility of the observed toxic effects resulting from overloading of the protein synthesis machinery of overexpressed heterologous ORF147 proteins in $E.$ $coli$ cells, a similar expression study was carried out with orf133 (SEQ ID NO:46), another existing upstream ORF in the CMS line, whose accumulation had no adverse effect on the growth of $E.$ $coli$. This suggests that such a characteristic of orf147 might also affect the development of floral organs. In previous reports, CMS-associated proteins such as PCF in $Petunia$, ORF125 in Kosena radish ($Raphanus$ $sativus$ cv. $Kosena$; Nivison et al., Plant Cell, 1989, 1, 1121-1130; Iwabuchi et al., Plant Mol. Biol., 199, 39, 183-188) and expression of orf 79 in BT-type CMS rice have been shown to be cytotoxic (Duroc et al., Biochimie, 2005, 87 1089-1100; Wang et al., Plant Cell, 2006, 18, 676-687).

Functional validation of the effect of the orf147 gene on male sterility using tapetum-specific expression of the orf147 gene in $A.$ $thaliana$ and $N.$ $tabacum$ transgenic plants in the present disclosure resulted in partial to complete male sterility, thereby suggesting that the encoded cytotoxic protein results in disruption of the development of male sporophytic and/or gametophytic cells.

The tissue-specific expression of orf147 not only disturbs the differentiation of stamens, but also affected the development of petals in the transgenic $Arabidopsis$ plants in the present disclosure, however no morphological differences were observed in the tobacco transgenic plants. This could possibly be due to a relatively weaker expression in the flowers under the influence of a heterologous $Arabidopsis$ promoter used for transformation experiments. The male sterile or semi-sterile $Arabidopsis$ as well as tobacco transgenic plants formed shortened stamen filaments. Interestingly, there were no notable differences in the vegetative growth of the transgenic plants and their wild type counterparts in both the tested plant species, which could be attributed to the specific interaction of CMS-associated genes with floral organs (Jing et al. J. Exp. Bot., 2012, 63, 1285-1295). The male sterile transgenic phenotype in both $Arabidopsis$ and tobacco was heritable and strong orf147 expression in the $T_1$ progeny indicated complete penetrance, an important finding in terms of research on the CMS mechanism in this pulse crop.

Overall, the present disclosure provides a novel isolated polynucleotide fragment of SEQ ID NO: 3 from pigeonpea, spatial heterologous expression of which in the mitochondria causes cytoplasmic male sterility (CMS). The disclosure further provides DNA constructs, and reagents, which can be used to generate transgenic plants to design CMS lines in crops with no previously available male sterile lines. This heritable and traceable fragment can be used to develop and maintain new hybrids across different plant species, and significantly reduces the time spent in identifying naturally occurring cytoplasmic male sterility factors.

We claim:

1. A DNA construct comprising a polynucleotide fragment, said polynucleotide fragment comprising a first sequence and a second sequence, wherein said first sequence encodes a mitochondrial transit peptide, said second sequence encodes a polypeptide having an amino acid sequence as set forth in SEQ ID NO: 1, and said polynucleotide fragment is operably linked to a flower or stamen specific promoter.

2. The DNA construct as claimed in claim 1, wherein said mitochondrial transit peptide is selected from the group consisting of a mitochondrial transit peptide of the cytochrome oxidase subunit IV from yeast, and a COX4 from *Saccharomyces cerevisiae* (P04037|1-25).

3. The DNA construct as claimed in claim 2, wherein said mitochondrial transit peptide amino acid sequence is as set forth in SEQ ID NO: 2, and is fused in-frame at the 5' end of said second sequence.

4. The DNA construct as claimed in claim 1, wherein said polypeptide is encoded by SEQ ID NO: 3.

5. The DNA construct as claimed in claim 3, wherein said mitochondrial transit peptide is encoded by SEQ ID NO: 4.

6. The DNA construct as claimed in claim 1, wherein said flower or stamen specific promoter is selected from the group consisting of an AP3 promoter for floral expression from *Arabidopsis*, an AP3 promoter for floral expression from Tomato, an AP3 promoter from *Coffea arabica*, a TA29 promoter for tapetum-specific expression from *Lycopersicon esculentum*, and a TA29 promoter from tobacco for tapetum-specific expression.

7. The DNA construct as claimed in claim 6, wherein said flower or stamen specific promoter sequence is as set forth in SEQ ID NO: 5.

8. A male sterile plant harboring in its genome a DNA construct as claimed in claim 1.

9. The plant as claimed in claim 8, wherein said plant is a dicot or a monocot.

10. An isolated polynucleotide fragment comprising a first sequence and a second sequence, wherein said first sequence encodes a mitochondrial transit peptide, and said second sequence encodes a polypeptide having an amino acid sequence as set forth in SEQ ID NO: 1.

11. The isolated polynucleotide fragment as claimed in claim 10, wherein said mitochondrial transit peptide amino acid sequence is as set forth in SEQ ID NO: 2.

12. The isolated polynucleotide fragment as claimed in claim 11, wherein said first sequence is as set forth in SEQ ID NO: 4, and said second sequence is as set forth in SEQ ID NO: 3.

13. The isolated polynucleotide fragment as claimed in claim 10, encoding a polypeptide having an amino acid sequence as set forth in SEQ ID NO: 6.

14. The isolated polynucleotide fragment as claimed in claim 13 having a sequence as set forth in SEQ ID NO: 7.

15. The isolated polynucleotide fragment as claimed in claim 10, wherein said fragment is derived from *Cajanus cajan* (L.) Millsp. (Pigeonpea).

* * * * *